(12) United States Patent
Shi

(10) Patent No.: US 12,296,332 B2
(45) Date of Patent: May 13, 2025

(54) MICRO-ASSAY CARTRIDGES

(71) Applicant: MicroPoint Bioscience Inc., Santa Clara, CA (US)

(72) Inventor: Yining Shi, Fremont, CA (US)

(73) Assignee: MicroPoint Bioscience Inc., Santa Clara, CA (US)

( * ) Notice: Subject to any disclaimer, the term of this patent is extended or adjusted under 35 U.S.C. 154(b) by 654 days.

(21) Appl. No.: 16/932,741

(22) Filed: Jul. 18, 2020

(65) Prior Publication Data

US 2021/0016275 A1  Jan. 21, 2021

Related U.S. Application Data

(60) Provisional application No. 62/876,170, filed on Jul. 19, 2019.

(51) Int. Cl.
| | |
|---|---|
| *B01L 3/00* | (2006.01) |
| *G01N 33/49* | (2006.01) |
| *G01N 33/86* | (2006.01) |
| *H01M 4/00* | (2006.01) |

(52) U.S. Cl.
CPC .... *B01L 3/502707* (2013.01); *G01N 33/4905* (2013.01); *G01N 33/492* (2013.01); *G01N 33/86* (2013.01); *B01L 2300/0636* (2013.01); *B01L 2300/0816* (2013.01); *B01L 2300/0864* (2013.01); *H01M 4/00* (2013.01)

(58) Field of Classification Search
None
See application file for complete search history.

(56) References Cited

U.S. PATENT DOCUMENTS

| | | | |
|---|---|---|---|
| 7,347,972 B1 | 3/2008 | Lee | |
| 8,961,903 B2 | 2/2015 | Sabada | |
| 9,347,931 B2 | 5/2016 | Killard | |
| 10,001,479 B2 | 6/2018 | Wan | |
| 2014/0014509 A1* | 1/2014 | Yan | C12Q 1/56 204/403.02 |
| 2018/0141039 A1* | 5/2018 | Reilly, III | B01L 3/502 |

OTHER PUBLICATIONS

Li, Hua, et al., "Correcting the effect of hematocrit in whole blood coagulation analysis on paper-based lateral flow device," Anal. Methods, 2018, 10, 2869-2874. (Year: 2018).*

* cited by examiner

*Primary Examiner* — Matthew D Krcha
(74) *Attorney, Agent, or Firm* — Westbridge IP LLC

(57) ABSTRACT

Provided are assay devices, methods and microfluidic cartridges for analysis of fluids, such as whole blood. A fibrinogen assay cartridge is adapted to measure whole blood flow rates on exposure to thrombin and measures hematocrit for a plasma fibrinogen calculation. Multiple channel cartridges are provided to allow determination of multiple assays (e.g., coagulation panel) from a single sample on a single cartridge.

8 Claims, 21 Drawing Sheets

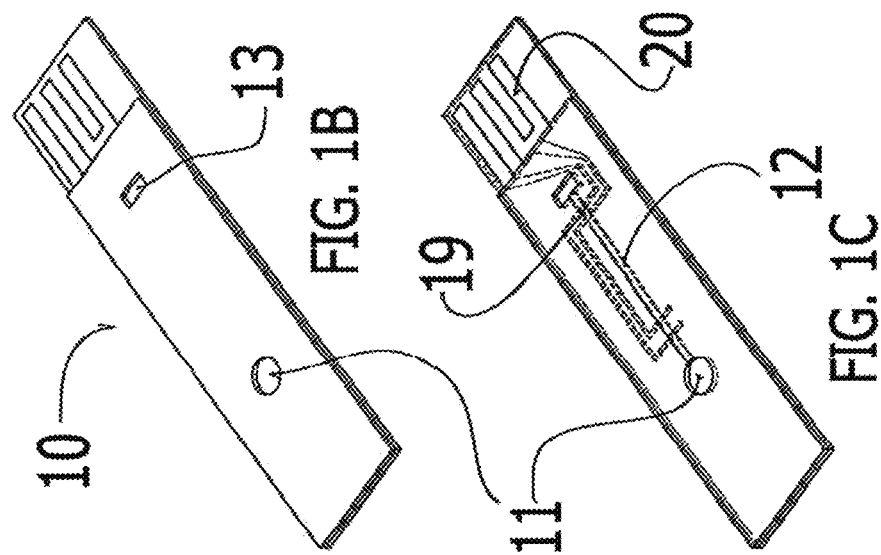
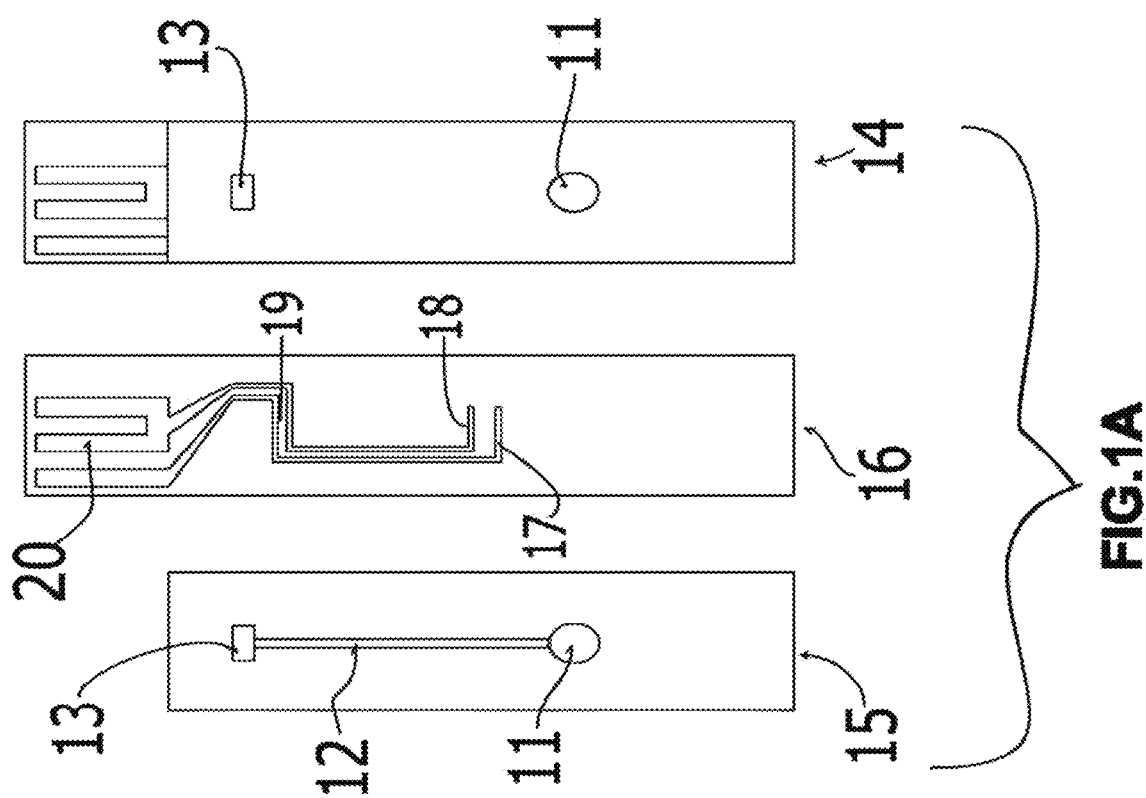

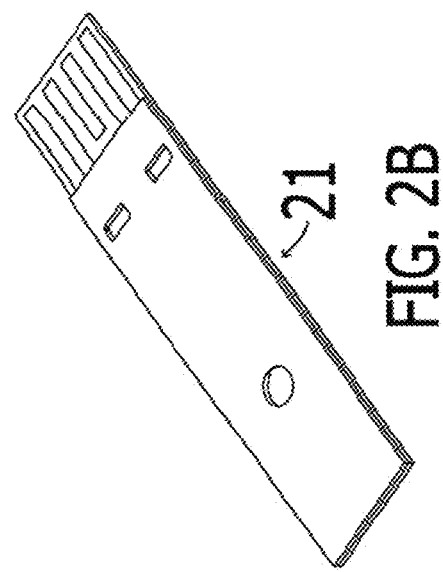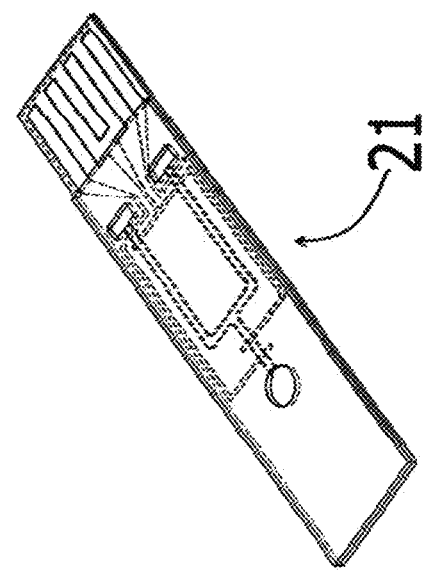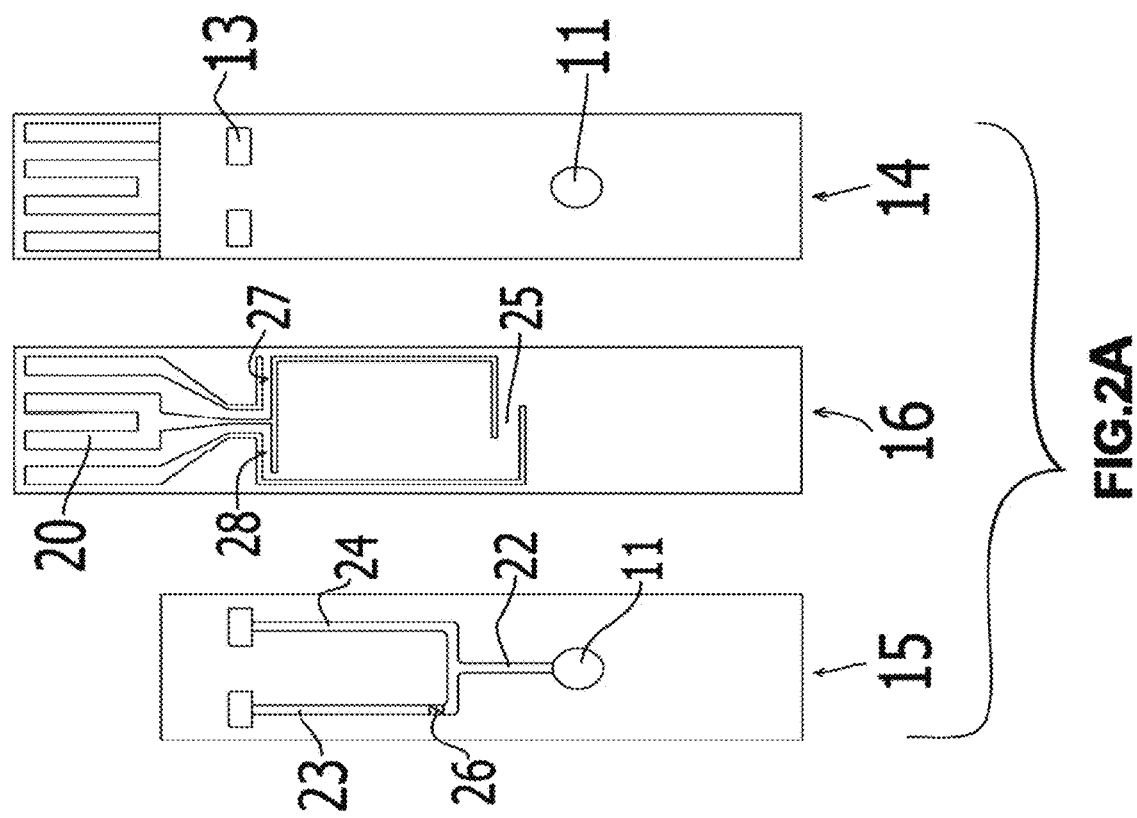

MICRO-ASSAY CARTRIDGES

FIELD OF THE INVENTION

The present inventions are in the fields of clinical microfluidic analysis cartridges and methods of use. The cartridges are typically assembled laminates with a single sample inlet port feeding one of more assay channels. Fibrinogen levels are determined directly from whole blood, e.g., in a single or two assay channel format. A 4-assay cartridge is configured to determine, e.g., a full coagulation panel at once from a small whole blood sample.

BACKGROUND OF THE INVENTION

For many clinical indications it is important to access the blood clotting system of the patient. Doctors can get an overview of a patient's coagulation system function by ordering a panel of assays, such as the prothrombin time (PT), activated partial thromboplastin time (aPTT), fibrinogen levels (FIB), and thrombin time (TT). Typically, this entails drawing a sample of anticoagulated blood, centrifugation to separate blood cells from plasma, and testing of clotting times of the plasma under a variety of conditions.

In Sadaba U.S. Pat. No. 8,961,903. PT/INR is measured relative to a control in a microfluidic cartridge. Coagulation time of plasma is measured based on a rate of plasma flow (fluid velocity) by an optical detector after addition of thrombin to the blood plasma. The device is only capable of measuring PT and not other coagulation parameters.

In Killard U.S. Pat. No. 9,347,931, fibrinogen by monitoring a change in flow rate of plasma exposed to excess thrombin across a surface of micropillars (see, e.g., FIG. 1C). Although the fibrinogen can be read on a hand held device from a microfluidic cartridge, the sample is plasma and relatively large amounts are required.

Fibrinogen can be determined using the Helena Laboratories coagulation analyzer CG02N. This technology employs iron oxide magnetic particles in an oscillating mag field with whole blood. As the blood clots, the magnetic particles become less free to oscillate in the magnetic field until an endpoint is reached. The endpoint time is proportional to the amount of fibrinogen in the blood. However, the whole blood sample for Analyzer CG02N must be inconveniently diluted with buffer by 5 times prior to test. Moreover, the fibrinogen calculation requires input of the blood sample hematocrit (Hct) value that is determined externally. Such a device is not convenient to use outside a clinical laboratory capable of Hct determinations.

In view of the above, a need exists for a device that can determine coagulation parameters on whole blood, without the need for input of external Hct data. It would be desirable to have a portable device that can determine fibrinogen, e.g., without the need for sample dilution or centrifugation. Benefits could also be realized through microfluidic cartridges than can determine a full coagulation panel from a single cartridge, e.g., with the sample coning directly from a patient finger stick. The present invention provides these and other features that will be apparent upon review of the following.

SUMMARY OF THE INVENTION

The novel technologies described herein include assay devices and methods for determining clinical results in a microfluidic format. The devices and assay methods employ cartridges, e.g., adapted to receive whole blood samples and/or provide a panel of analyte determinations from the same sample in a portable reader. For example, the versatile devices can read accurately controlled coagulation results from a single whole blood sample, e.g., from cartridges branching to four or more reagent/detection channels.

In one embodiment of fibrinogen assay cartridge, there are timing electrodes and impedance detectors configured to determine a viscosity and a hematocrit. The cartridge can include, e.g., a sample inlet in fluid contact with a first channel and a second channel. The first channel has a thrombin reagent and a timing electrode, the second electrode can include a pair of electrodes adapted to detect impedance across the channel. A sample fluid (e.g., whole blood, whole blood from a finger stick, whole blood without anticoagulant, or whole blood anticoagulated with citrate) transit time to flow past the thrombin reagent (e.g., coated on a channel surface such as the top and/or bottom surface) to the timing electrode of the first channel can be proportionate to the amount of fibrinogen in the sample. A measure of sample impedance or resistance across electrodes of the second channel can be directly proportionate to amount of particles (e.g., RBCs) in the sample. That is, the impedance or resistance measured across the pair of electrodes can provide a particle volume parameter (e.g., Hct) for the sample, and the time for the sample to flow to the timing electrode can provide fibrinogen quantitation for the sample fluid. A cartridge reader can detect and interpret, e.g., the whole blood hematocrit/fibrinogen, and calculate a blood plasma fibrinogen value with enhanced accuracy.

In a preferred arrangement, the cartridge channels are lateral flow channels with an inlet channel flowing from the sample inlet to first and second channel branches. The cartridge can have a start electrode, e.g., to detect initial (start) flow of the sample and the timing electrode can detect (end) the sample some distance down the first channel. In this way, the flow of sample can be detected and timed as it flows between the start and timing electrodes. The sample comes in contact with a thrombin reagent near the channel entrance. Samples with higher fibrinogen, at a given hematocrit, will have longer transit times between electrodes than samples with lower fibrinogen levels. Optionally, the cartridge can include a control channel with a control timing electrode (but no thrombin) so that a timing value representing zero fibrin conversion can be obtained, e.g., to enhance accuracy and sensitivity of fibrinogen calculations of the assay device receiving the cartridge.

The cartridge is typically inserted into a reading device, making connections between the cartridge sensors and a digital computer (processing unit) of the device and/or presenting a detection chamber for interrogation by external sensors (e.g., optical detectors using LEDs and photosensitive diodes). For example, the electrodes can be in electrical contact with a processing unit through contact pads. The processing unit can actuate electrodes and detect impedance between impedance electrodes, e.g., to determine a percent particles of the sample. Similarly, the processing unit can receive signals as the sample front contacts timing electrodes, e.g., for key data in the determination of fibrinogen value for the sample.

The processing unit can be adapted to calculate a fibrinogen value for the sample, e.g., based on the transit time for a control blood sample (e.g., a standard regression curve). However, it can be preferable that the fibrinogen value account for the percent particles (e.g., particle volume, known hematocrit, or hematocrit determined by the impedance electrode technique) in the sample. For example, the viscosity value (e.g., transit time between timing electrodes)

can be adjusted for interference by particles using an available hematocrit. Further, the plasma fibrinogen value can be adjusted by removing the excluded volume of the cells that may be present in the whole blood sample. These calculations can be achieved, e.g., using an algorithm or data table resident in the processor to adjust the value.

Methods of determining fibrinogen in a whole blood sample can take advantage of the cartridges and assay devices described herein. For example, a fibrinogen assay for whole blood or plasma can start by applying a sample to the microfluidic cartridge sample inlet in fluid contact with a first channel and a second channel, wherein the first channel comprises thrombin and a timing electrode and the second channel comprises a pair of electrodes adapted to detect impedance across the channel. The cartridge interacts with the assay device processor to determine a time taken for the sample fluid to flow to the timing electrode of the first channel, and to measure an impedance or resistance of the sample in the second channel. The sample is applied to the sample inlet of the cartridge, to flow from the inlet into the first channel by capillary action, contacting the thrombin, thus initiating conversion of any sample fibrinogen to fibrin. Conversion of fibrinogen to fibrin substantially increases the fluid viscosity to slow flow of the fluid in the first channel. The processor determines the time it takes the sample to flow along the first channel from a start electrode to the timing electrode. This value is proportionally related to the amount of fibrinogen in the sample. Meanwhile, sample fluid also flows from the inlet into the second channel by capillary action to contact the paired electrodes (e.g., on opposite sides of the channel) to measure an impedance or resistance of the fluid. If the particles suspended in the fluid conduct electric current differently from the fluid (as do blood cells), the impedance/resistance can be related to the ratio of fluid to particle volume, e.g., determining a hematocrit for the sample based on the measured impedance across the paired electrodes. A fibrinogen value for the whole blood sample can determined based on the detected flow time, and a fibrinogen value for the excluded fluid (e.g., plasma) can be determined by adjusting the whole blood fibrinogen value based on the determined hematocrit. Since the flow time of sample is also proportionally related to the levels of hematocrit in sample, the second channel can be used as a reagent negative control channel with, e.g., timing electrodes, but no thrombin reagent, to counteract or offset the effect of hematocrit on fibrinogen determination by the first channel. In other words, the flow rate without thrombin and fibrin formation can be considered (e.g., subtracted or ratio normalized) to determine the flow difference related to the sample fibrinogen concentration.

In another aspect, the cartridges can include two, three, four, or more assay channels, e.g., receiving sample from the same sample inlet. The channels can be configured to run a variety of different assays and controls on the same sample. For example, a multi-assay cartridge can include a first layer having a first lateral flow channel and a second lateral flow channel, a second layer comprising a third lateral flow channel and a fourth lateral flow channel, with a third layer located between and separating the first and second channel layers. The channels are aligned in parallel planes to each other, e.g., the layers being plastic sheets laminated together. The channels are typically capillary channels, e.g., dimensioned and surfaced to promote a desired flow of sample by capillary action. The sample inlet is in fluid contact with first channel, second channel, third channel and fourth channel, e.g., wherein the inlet runs vertically through the layers to intersect feeder channels to the channels in the same layer. Each channel can have one or more bioactive reagents and an electrode (or no reagents, e.g., in some negative controls). The cartridge can be configured to receive a sample fluid into the sample inlet, which flows separately into the first layer and second layer channels to contact, e.g., the bioactive reagents and electrodes. Different assays can be carried out in each channel, e.g., to provide a chemistry panel, coagulation panel, and/or the like.

In one embodiment, the first and second channels branch from a first main channel in the first layer in contact with the sample inlet, and the third and fourth channels branch from a second main channel in a separate layer in contact with the sample inlet. A third layer can include electrodes in electrical contact with external contact pads adapted to provide conductive contact with wiring of the assay device processor. Top and bottom cover layers can be provided, or the outside layers can have channels that do not penetrate the whole thickness of the layer. The conductors and or/contact pads for the first and second channel electrodes can be configured on opposite sides of the third layer from conductors for the third and fourth channel electrodes. The electrode in one or more of the channels can be configured to detect, e.g., impedance change, capacitance change, and/or conductance change, e.g., to provide timing or to characterize a sample. In an embodiment, one of the channels contains thrombin and a pair of electrodes separated along the channel to time a flow of the sample fluid between the electrodes.

The channels can include bioactive agents or other reagents, e.g., that interact with sample analytes of interest to characterize their activity and/or signal their presence. Samples are typically whole blood, whole blood anticoagulated with citrate, plasma, plasma anticoagulated with citrate, and/or the like. The samples may be cell culture fluid or other body fluids besides blood. In the context of coagulation assays, the bioactive reagents in the cartridge channels can include, e.g., tissue factor, an intrinsic pathway activator, thrombin, thromboplastin, calcium, and/or the like. The reagents can be presented to the sample flow, e.g., in the form of a dry film on a channel wall, e.g., a dry film on a top surface and a bottom surface of the channel.

During an analysis, the cartridge can be located in functional (e.g., electrical and/or optical) contact with an assay device comprising a processing unit. The processing unit is typically a digital processor with inputs from sensors, outputs to actuators, and a user interface. The assay device can include a temperature control unit adapted to hold the cartridge at a designated temperature.

In a particular method, the cartridge can have multiple channels to determine, e.g., a panel of four clinical values. For example, an assay cartridge can be provided with a first layer having a first lateral flow channel and a second lateral flow channel, a second layer comprising a third lateral flow channel and a fourth lateral flow channel, and a third layer located between and separating the first and second layers; the sample inlet being in fluid contact with the first channel, second channel, third channel, and fourth channel. The layers are aligned in parallel planes to each other. The channels include one or more bioactive reagents and/or an electrode. The cartridge is configured to receive a sample fluid into the sample inlet, which flows separately into the first layer and second layer channels to contact the bioactive reagents and electrodes. Sample fluid is applied to the sample inlet and flows from the inlet into the first and second channels of the first layer, and flows into the third and fourth channels of the second layer, e.g., bringing the sample fluid into contact with the bioactive reagent and/or electrodes in each channel. An electric parameter is detected, e.g., through electrical contact of the electrodes with the assay device processor. The four clinical values are calculated based on the detected electric parameter. For example, the clinical values can be coagulation parameters such as PT, aPTT, TT, and fibrinogen.

Definitions

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification, the singular forms "a", "an" and "the" can include plural referents unless the content clearly dictates otherwise. Thus, for example, reference to "a surface" can include a combination of two or more surfaces; reference to "cells" can include mixtures of cells, and the like.

Unless defined otherwise, all technical and scientific terms used herein have the same meaning as commonly understood by one of ordinary skill in the art to which the invention pertains. Although any methods and materials similar or equivalent to those described herein can be practiced without undue experimentation based on the present disclosure, preferred materials and methods are described herein. In describing and claiming the present invention, the following terminology will be used in accordance with the definitions set out below.

As used herein, peripheral edges of planar cartridge elements are the thin surfaces exposing the thickness of the element, e.g., as in common usage of the term. As used herein, directional terms, such as "upper", "lower", "top", and "bottom" are as in common usage, e.g., with a planar cartridge disposed resting upon a table with the top cover above the base section. Height, width, and depth dimensions are according to common usage, e.g., with reference to a cartridge major plane in a horizontal attitude.

As used herein, the term "microfluidic" refers to systems or devices having a fluid flow channel with at least one cross sectional dimension less than 1000 µm. Most microfluidic channels allow capillary flow, e.g., depending on the affinity of a particular fluid for the channel walls. Some functional capillary scale channels can be greater than microfluidic scale. A microfluidic channel can have a cross-sectional dimension of 1000 µm, or less, 500 µm or less, 300 µm or less, 100 µm or less, 50 µm or less, or 10 µm or less. In many embodiments, the channel dimension is about 50 µm to 100 µm, but typically not less than 1 µm. Most microfluidic channels are capillary channels owing to their dimensions within the capillary geometry contact angles of typical liquids. This can, of course, depend on the affinity (e.g., contact angle) between the channel surface and the particular fluid. Capillary channels can have a least cross-sectional dimension of more than 1 mm, but this is not typical. Capillarity is a general term referring to phenomena attributable to the forces of surface or interfacial tension. A capillary scale chamber or channel has at least one dimension that functionally results in flow of an intended fluid along the chamber or channel surface by capillary action. Capillary scale chambers and channels of the invention can be at a microfluidic scale or not. Capillary flow can exist in channels with no microfluidic scale dimension, e.g., where the affinity for the fluid and surfaces are high, and/or the channel includes a porous material presenting smaller dimensioned topography. However, in the current inventions, the capillary scale dimension in the capillary channels is typically the height dimension, e.g., while the width dimension can be substantially larger.

As used herein, "substantially" refers to largely or predominantly, but not necessarily entirely, that which is specified.

The term "about", as used herein, indicates the value of a given quantity can include quantities ranging within 10% of the stated value, or optionally within 5% of the value.

A prothrombin time (pro-time, PT) is as understood in the art of clinical pathology. The PT, along with its derived measures of prothrombin ratio (PR) and international normalized ratio (INR), are assays used to evaluate the extrinsic pathway and common pathway of coagulation (see, e.g., FIG. 15). In a typical lab bench prior art PT assay, citrate anticoagulated plasma is held at 37° C. At time zero, an excess of calcium and tissue factor is added to initiate clotting. The clotting time endpoint can be measured in a variety of ways, typically be detecting a viscosity value confirming a certain level of clot formation. The PT assay devices and methods described herein are configured to determine PT values that correlate with those of old art standard determinations (often providing PT values directly from a whole blood sample).

The partial thromboplastin time (PTT) as known in the prior art is a blood test similar to the PT, but adapted to measure the intrinsic clotting pathway. Partial thromboplastin time is typically analyzed in an automated instrument at 37° C. The test is termed "partial" due to the absence of tissue factor from the reaction mixture. Citrate anticoagulated whole blood is centrifuged to obtain plasma. At time zero the plasma has been mixed with calcium (e.g., in a phospholipid suspension). The intrinsic pathway is activated with an activator (such as kaolin) and a clotting time is determined by mechanical or optical end point detection. The PTT devices and methods described herein are configured to determine PTT values that correlate with those of old art standard determinations.

The thrombin time (TT) as known in the art is an assay testing the end of the common pathway, wherein an excess of thrombin with calcium is added to anticoagulated plasma and the time to clot noted. The TT devices and methods described herein are configured to determine TT values that correlate with those of old art standard determinations.

Fibrinogen assays are used to quantitate fibrinogen in a patient's blood. Many fibrinogen assays employ techniques similar to the thrombin time, but are configured to provide data proportional to fibrinogen quantity. For example, the Clauss assay is a typical fibrinogen assay wherein a high concentration of thrombin is added to dilute test plasma and the clotting time is measured. The fibrinogen value is read off a standard reference calibration curve. The FIB devices and methods described herein are configured to determine fibrinogen values that correlate with those of old art standard determinations.

A processing unit is an element of the assay device, e.g., that reads cartridges of the invention. The processing unit is typically includes a digital computer, microcomputer, or integrated circuit, as understood in the art. The processing unit has electronic inputs to receive electronic parameters (e.g., from cartridge electrodes, interrogating photodiodes, etc.) or to receive data from accessory circuits (such as, e.g., user interface or cartridge information). The processing unit has output circuits, e.g., to actuate accessories, energize sensors, or update the user interface.

A "cartridge" is as known in the field of sample analyses. Typically, cartridges of the invention are microfluidic chips comprising channels, chambers, electrodes, adapted interact with a sample and provide a signal correlated with a sample analyte of interest, as described herein. The cartridge is adapted to be functionally received in a contact with an assay device, e.g., to allow interactions with a processing unit energizing and receiving information from cartridge sensors.

Reagents are as known in the art of clinical analysis. Reagents in the cartridges of the invention typically interact with samples to provide reaction conditions and/or to detectably interact (e.g., react or catalyze change) with analytes of interest in a sample, e.g., providing a signal detectable by sensors of the cartridge.

Samples, in the context of the present assay devices and cartridges are typically liquids of interest containing one or more analytes of interest. Typical samples for analysis in the present cartridges can include, e.g., whole blood, plasma, other body fluids of an animal, and/or sample fluids from a manufacturing process.

BRIEF DESCRIPTION OF THE DRAWINGS

FIGS. 1A, 1B, and 1C present schematic diagrams of a laminated single channel fibrinogen assay cartridge. FIG. 1A shows the separated layers of a cartridge.

FIG. 1B shows a top view of an assembled cartridge and FIG. 1C shows an internal reveal view of the assembled cartridge.

FIGS. 2A to 2C present schematic diagrams of a laminated dual channel fibrinogen assay cartridge, including a flow rate control channel. FIG. 2A shows the separated layers of a cartridge. FIG. 2B shows a top view of an assembled cartridge and FIG. 2C shows an internal reveal view of the assembled cartridge.

FIG. 9A shows a time course of normal and abnormal fibrinogen samples in a FIB cartridge. FIG. 9B shows close up images of test channels of a FIB cartridge with samples having no fibrinogen, abnormal fibrinogen, and normal fibrinogen.

FIG. 21A presents data without hematocrit adjustment, while FIG. 21B presents data adjusted for hematocrit.

DETAILED DESCRIPTION

Figure 3:
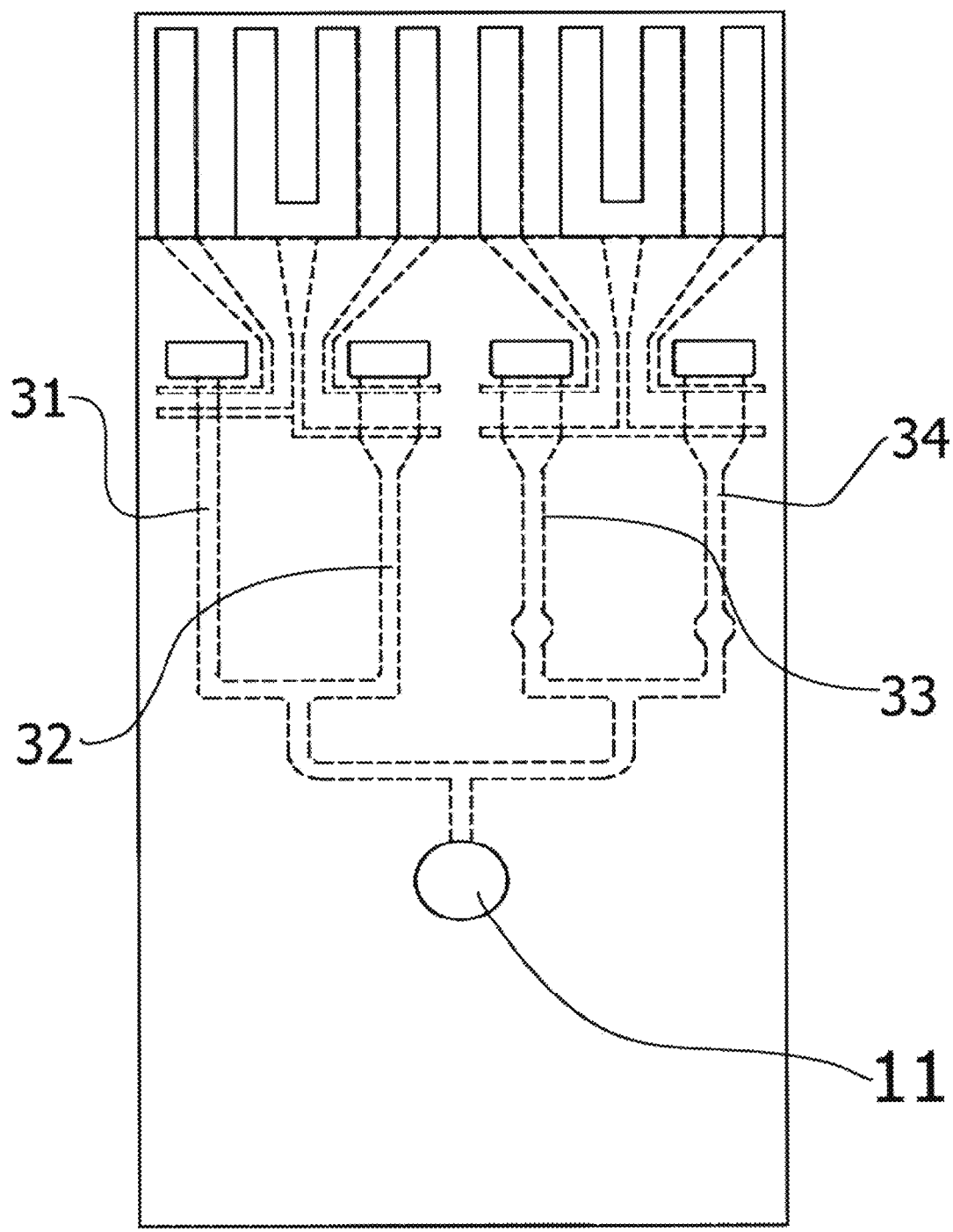
FIG. 3 shows a schematic diagram of a 4-channel assay cartridge, e.g., configured to determine a coagulation panel result set.

The techniques, devices, and methods described herein are improvements over prior clinical assay technologies, e.g., allowing coagulation assays on small amounts of whole blood. The fibrinogen assay cartridges are configured to receive whole blood sample, e.g., flowing through paired capillary channels to determine sample flow rate and impedance. The cartridge is adapted so that the impedance is related to the percentage plasma in the sample, and the flow rate is related to the amount of fibrinogen in the plasma. Such a fibrinogen assay can be incorporated into a cartridge further housing a variety of additional channels and reagents to determine a panel of related clinical parameters of interest.

Methods of determining fibrinogen provide the important benefit of determining plasma fibrinogen directly from whole blood, without the need to remove blood cells and/or perform sample dilution. For example, the methods can include provision of a specialized microfluidic assay device, e.g., having a channel for determining sample particle volume and a channel for determining an amount of fibrinogen. A liquid sample is applied to an input port to flow into each channel. Active thrombin is in the first channel, which begins conversion of sample fibrinogen into fibrin. A flow start is noted and the sample flows a distance in the channel to a timer electrode. The time to reach the timer electrode is, e.g., proportional to the amount of fibrinogen and hematocrit levels in the original sample. Sample flows in a second channel, e.g., to a chamber between electrodes where measured resistance to electric current is proportional to the volume of particles suspended in the sample fluid. Sample in the second channel can optionally act as a no thrombin flow rate negative control.

In another embodiment, a cartridge includes three layers, e.g., with the second layer separating the first and third layers each having two channels and in fluid contact with a common sample input port. Different assay configurations can be arranged in each channel, e.g., so that four or more different assays can be run in the same cartridge. The cartridge can be placed in an assay device to contact conductors and/or present reaction chambers for interrogation, e.g., providing input to assay device processors for interpretation of sample characteristics and/or analyte quantity.

In one method of using the three-layer/four-channel cartridge, the channels can have certain bioactive molecules that interact with the sample to signal the presence, quality, and/or amount of four different parameters and/or analytes in a sample. For example, the channels can run four assays of a coagulation panel, e.g., PT, aPTT, TT, and fibrinogen.

Fibrinogen Assay Systems for Whole Blood Samples.

A fibrinogen cartridge can be configured with a microfluidic flow channel, e.g., having a start timing gate and a finish timing gate. Active thrombin is located near the proximal end of the channel and blood sample (or plasma) fibrinogen begins to clot from fibrin formation on contact. The more fibrinogen, the more viscous the sample becomes, and the slower the sample progresses along the channel. The time between the start and finish timing gates is proportional to the sample fibrinogen content. The cartridge can have a second channel with timing gates, but no thrombin, to act as a negative control. Electrodes in a cartridge channel can measure impedance of the sample, e.g., to determine a ratio of sample particles to sample fluid.

A basic fibrinogen cartridge design can provide fibrinogen and hematocrit determinations using timing gates and impedance electrodes along a single lateral flow channel. As shown in FIG. 1A, the fibrinogen cartridge 10 includes a sample inlet port 11 in fluid contact through lateral flow channel 12 to vent 13. The laminated design, simplified here includes top layer 14, middle channel layer 15, and bottom electrode layer 16. Laminated together, as shown in FIGS. 1B and 1C, sample can be applied to inlet 11 and flow along channel 12, coming in contact with timing gate electrodes 17 and 18 to start a flow timing sequence. Further, the impedance across electrodes 17 and 18 in the presence of the sample is related to the amount of particles in the sample and can be detected to determine, e.g., a hematocrit of a whole blood sample. The time it takes the fluid (liquid) sample to flow through the channel can be marked by contact of the fluid with the electrodes at end timing gate 19.

In use, the single channel cartridge 10 is typically loaded into a portable assay device (not shown) providing a temperature controlled environment, establishing electrical contacts between the cartridge and device through contact pads 20. While the cartridge is in the assay device, a droplet of whole blood is placed in the inlet port 11, from a pipette or directly from a patient finger stick, and flows by capillary action to contact thrombin reagent and contacting the starting gate electrode pair 17/18, initiating a timer start. Detection of sample contact with the electrodes can be practiced using techniques known in the art, e.g., detecting electric current flow between electrodes 17/18 or detection of a capacitance change, e.g., as the sample contacts an individual electrode. With the sample across the starting gate electrodes 17/18, the processor (through accessory electronic detector) can detect an impedance or resistance of the sample across the electrodes. This impedance or resistance is directly related to the amount of (e.g., less conductive) particles suspended in the sample fluid, and so can be used to calculate, e.g., a hematocrit of a whole blood sample. When the sample flow reaches end timing gate 19 there is a detectable change in the resistance between the conductor electrodes (17 and/or 18, and gates 19), and the processor thereby detects an end time for calculation of a total flow time between start and end gates. The total flow time is related to the viscosity of the sample fluid, e.g., amount of fibrinogen, and the hematocrit levels in the sample.

A dual channel cartridge design can further improve accuracy and precision of the assay. A negative control channel can branch from the initial inlet flow channel, as shown in FIG. 2. The layout of the dual channel fibrinogen cartridge has many aspects similar to the single channel design, but the main input channel branches to provide a control channel. The dual channel cartridge 21 includes a sample inlet port 11 in fluid contact with vents 13 through inlet channel 22 and lateral flow channels 23 and 24. The dual channel cartridge can be assembled from 3 or more layers (top/channel/electrode) in a fashion similar to that described for the single channel design. Sample can be applied to inlet 11 and flow along inlet channel 22 before branching to matching test 23 and negative control 24 channels. Flow timing start is initiated when the sample crosses $T_0$ timing gate 25. The impedance of the sample across the electrodes of the To timing gate 25 is detected by the processor unit through contact pads 20 and used to calculate the hematocrit of the sample. Thrombin reagent 26 is present in the test channel 23 but not in the negative control channel 24. The time it takes the fluid (liquid) sample to flow through the channels can be marked by contact of the fluid with the electrodes at test $T_1$ timing gate 26 and control $T_2$ timing gate 27.

In use, the dual channel cartridge 21 is loaded into a portable assay device (see, e.g., FIG. 7B), establishing electrical contacts between the cartridge and assay device processing unit through contact pads 20. A whole blood sample is applied to inlet port 11 and flows by capillary action across the $T_0$ timing gate 25 and along the inlet channel 22 before branching into the matching test 23 and control 24 channels. Sample flowing along the test branch 23 contacts thrombin 26 initiating conversion of fibrinogen to fibrin, thereby increasing the viscosity of the sample and slowing progress along the channel to test T timing gate 28. Sample flowing along the control branch 24 does not contact thrombin and retains initial viscosity as it flows on to control $T_2$ timing gate 27.

The processor has received inputs from the $T_0$ timing gate 25 to evaluate the sample hematocrit and to note the flow start time. The processor receives inputs from the test $T_1$ timing gate 28 and control $T_2$ timing gate 27 to note the test and control end times.

The difference between the test and control flow times represents the net effect of fibrinogen (converted to fibrin) on flow time of the sample, as illustrated below:

$T_1$=Flow time$_{test\ channel}$∝(Flow impedance fibrin formation+Flow impedance$_{hematocrit}$)

$T_2$=Flow time$_{control\ channel}$∝(Flow impedance$_{hematocrit}$)

$\Delta T=(T_1-T_2)$∝(Flow impedance$_{fibrin\ formation}$)

The sample impedance at the $T_0$ timing gate 25 is related to the hematocrit (percent particles) of the sample. The fibrinogen of the sample can be determined from a standard curve of time versus fibrinogen content or from a lookup table. A plasma (whole blood minus cells) fibrinogen value can be calculated, e.g., as the whole blood fibrinogen value over the proportion of plasma or:

Plasma Fib=WB Fib/((100−Hct)/100)

The useful range of fibrinogen determinations for a cartridge can be expanded, e.g., by providing different reaction kinetics in different assay channels. For example, to extend the fibrinogen measurement range for a cartridge, the dual channel design of FIG. 2 can be configured so that both channels 23 and 24 are sample test channels. That is, channels 23 and 24 can have different amounts of thrombin reagent, e.g., with channel 23 having less thrombin than channel 24 for a useful assay range shifted to lower fibrinogen concentrations. This concept is further expanded and outlined in FIG. 13 and Example 9, below.

In another aspect, the assay cartridges and methods can be configured to provide assays for two or more analytes on the same cartridge. For example, as shown in the four assay cartridge of FIG. 3, a coagulation panel of PT, aPTT, Fibrinogen, and TT can be laid out across a single cartridge, with a single sample inlet port. For example, the cartridge can have an inlet port 11 branching to a PT assay channel 31, aPTT channel 32, Fibrinogen channel 33, and TT channel 34.

Figure 4:
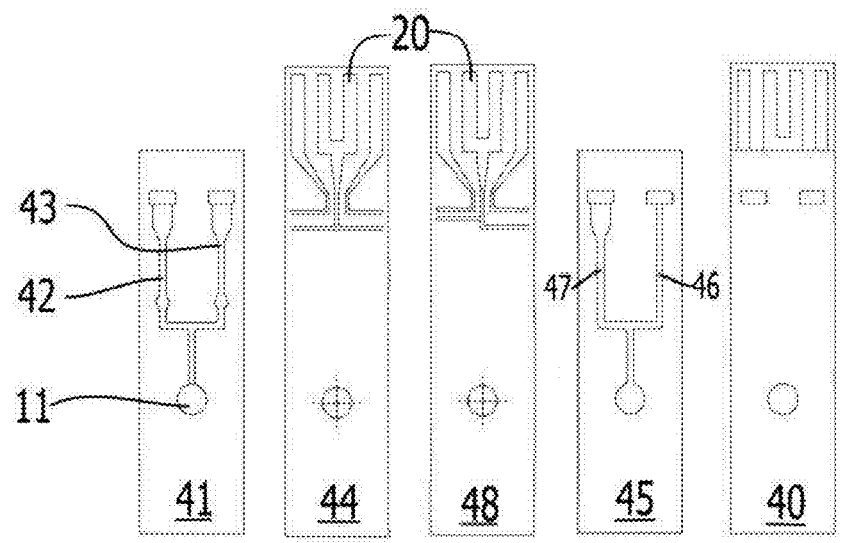
FIG. 4 shows schematic diagrams of a four-channel cartridge. The five cartridge layers are configured for laminated assembly into a double sided cartridge having 4 assay channels receiving sample from a single sample inlet port.

Alternately, a 4-assay cartridge can be configured to have 2 assay channels in an upper channel layer and 2 more channels in a lower channel layer. In this way the cartridge can be as narrow as 2-assay cartridges and adapted to fit into the same assay device docking area. Further, the 2-sided configuration can present more electrodes and assay detection windows/electrodes to alternate detection devices of the assay device. For example, as shown in FIG. 4, the cartridge can comprise a top layer 40, a first assay channel layer 41 (delineating a first assay channel 42 (e.g., PT) and a second assay channel 43 (e.g., aPTT)), and a first electrode layer 44 configured to detect assay results for the first assay channel layer. Further, the cartridge can include a second assay channel layer 45 delineating a third assay channel 46 (e.g., fibrinogen) and a fourth assay channel 47 (e.g., TT), and including a second electrode layer 48. This is discussed further in Example 3 of this specification.

Figure 5:
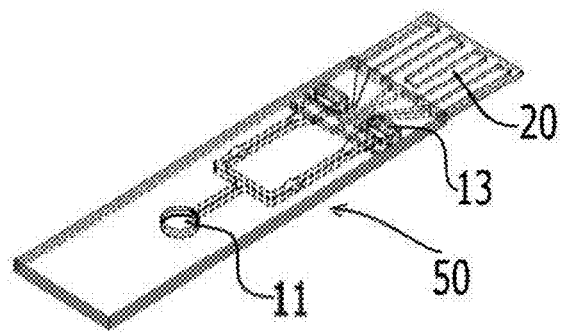
FIG. 5 shows an assembled double sided 4-assay cartridge.

The 5-layered 4-assay cartridge can be laminated together as shown in FIG. 5. Assembled cartridge 50, has sample inlet port 11 and vents 13 visible on the top surface. Electrode contact pads 20 for the upper two assays are visible. The reveal presentation of FIG. 5 shows some detail on the cartridge layer structure. Note that the sample inlet goes through all but the bottom electrode layer to provide fluid flow contact with inlet channels to all four assay channels. The vent ports 13 likewise service assay channels on both first and second assay channel layers. The electrode contact pads for the assay channels of the lower second assay layer channels are back (bottom) side of the second electrode layer.

Figure 6:
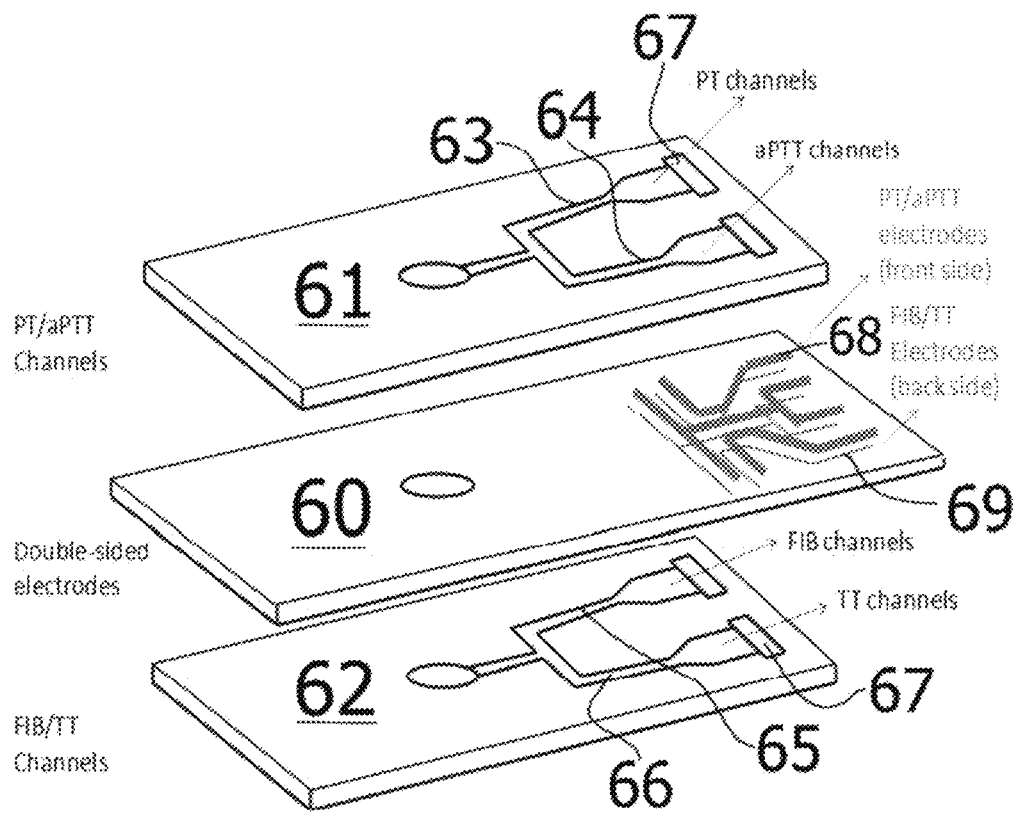
FIG. 6 show an example of channel and electrode cartridge layers configured to determine four different parameters of a coagulation panel.

As shown in FIG. 6, the electrode layer can be two-sided, so that the top side electrodes contact the channels of the top channel layer and the bottom electrodes contact the bottom channel layer. The two-sided electrode layer can present electrode contact pads (to the processor unit) on opposite sides or on the same side of the electrode layer. This is discussed further in Example 3, below.

Typical cartridge dimensions include a length of about 6 cm and a width of about 2 cm and a thickness of about 0.7 mm. The depth through the laminated layers can be from less than about 0.3 mm to more than about 3 mm, from 0.5 mm to 2 mm, from 0.7 mm to 1.5 mm, or about 1 mm. For example, the cartridges can have a length ranging from more than 10 cm to less than 2 cm, from 8 cm to 3 cm, from 7 cm to 5 cm, or about 6 cm. The cartridges can have a width ranging from more than 4 cm to less than 0.5 cm, from 3 cm to 1 cm, from 2.5 cm to 1.5 cm, or about 2 cm.

Cartridges typically have at least 2 layers to about 10 layers. For example, 3 layers (e.g., top/channel/bottom), 4 layers (e.g., top/channel/electrode/bottom), 5 layers (e.g., top/channel/electrode/channel/electrode or top/channel/2-sided electrode/channel/bottom), 6 layers (e.g., top/channel/electrode/channel/electrode/bottom, or top/electrode/channel/separator/channel/electrode).

The cartridges are thin, depending on the number of layers required. The cartridges can have a thickness (depth) ranging from more than 2 mm to less than 0.2 mm, from 1 mm to 0.3 cm, from 0.6 mm to 0.4 mm, or about 0.5 mm. A typical cartridge has laminated layers, though manufacture can be unitary, e.g., by molding, micro-machining, 3D additive manufacturing, and/or the like. The channel layer, containing the voids defining the channel cross sections are often the thinner layers, while the bottom (base) layer is often the thickest layer, and the top (cover) and electrode layers are often intermediate in thickness. The base layer can be somewhat thinner, when a detection (e.g., by photometry) is through the base. In one embodiment, the cover layer is about 175 μm thick, the channel layer about 80 μm, the electrode layer about 100 μm, and the base layer about 250 μm. The channel layer can have a thickness ranging from more than about 1 mm to less than about 0.04 mm, from 500 μm to 60 μm, or about 100 μm. It is preferred that the cover and base layers be thicker than the channel layer, to provide the physical strength and minimize channel deformation, e.g., when the cartridge happens to be flexed. However, where conditions require the channel layer to be thicker, thinner overall depth can be retained by employing thinner base and cover layers.

The layers of the cartridge can be of the same material, or a combination of materials. The cartridge layers can comprise plastic, glass, metal, ceramic, and/or the like. However, the bulk of the cartridges, and most typical layer materials are plastics. For example, polyethylene terephthalate (PET), polyethylene (PE), polyvinyl chloride (PVC), low-density polyethylene (LDPE), polypropylene (PP), polystyrene (PS), and the like. Due to its flexibility, inertness, and light transmission, a preferred plastic for flexible cartridge layers is PET. The assembled cartridge is configured to have a flexibility modulus of 1.5 GPa or less, 1 GPa, 0.5 GPA, 0.25 GPa, 0.1 GPA, or less.

Assay Devices and Systems

Figure 7A:
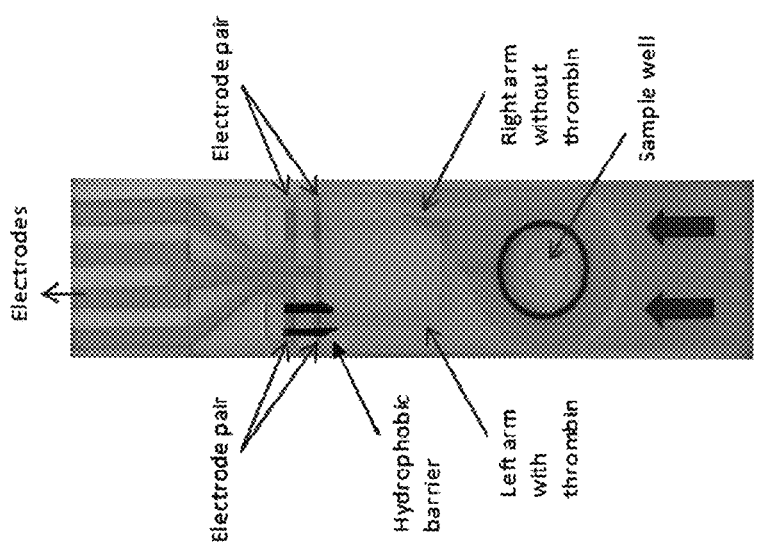
FIG. 7A shows a cartridge configured for a controlled fibrinogen assay.
Figure 7B:
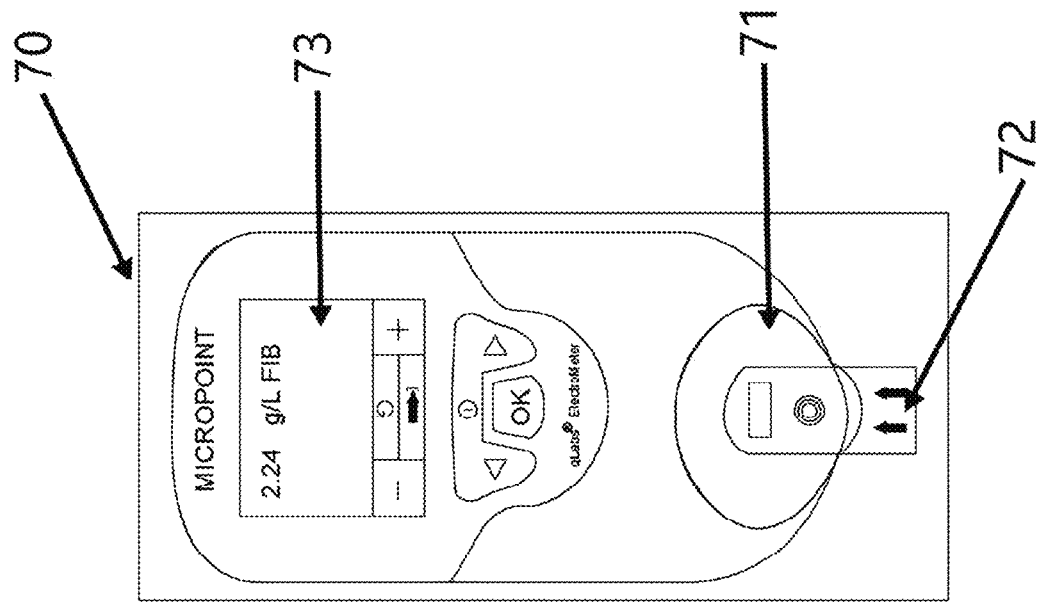
FIG. 7B shows an assay device adapted to receive the fibrinogen cartridge.

The present assay devices include the assay cartridges described herein functionally interacting with a processing unit. The assay device can hold the cartridge, providing necessary electrical contacts between the cartridge and processing unit (e.g., digital computer), e.g., for controlling outputs and detecting inputs. The assay device 70, e.g., as shown in FIG. 7B can be a hand held device with a docking area 71 receiving a cartridge 72. The assay device can have a user interface 73, e.g., for user inputs top the processing unit and processor output of assay results. FIG. 7A shows an image of a fibrinogen assay cartridge (FIB cartridge) that is inserted into the Electrometer through the docking area shown in FIG. 7B.

The processing unit can receive a variety of inputs. For example, the processing unit can receive user instructions from the user interface, and it can receive information (e.g., sample ID, patient ID, test type, cartridge type) from an inserted cartridge. The processing unit can be in electrical contact with the cartridge to receive electrical inputs (e.g., resistance, amperage, capacitance, voltage, impedance) from cartridge electrodes contacting fluids during an assay. For example, the processing unit can be in contact with channel electrodes acting as timing gates or detectors of fluid characteristics. The processor can receive inputs of other detectors, such as temperature sensors and photodetectors.

The processing units can control outputs to energize actuators, environment controls, and detector components. The processing unit is typically digital and can receive digital input, e.g., from accessory sensors in contact with cartridge electrodes. For example, the processing units can receive data from temperature sensors and output instructions (e.g., to a thermoelectric device) to maintain a programmed temperature for an assay. The processing unit can instruct application of a desired voltage to cartridge electrodes. The processing unit can output information requests or data (e.g., assay result) output to the user interface.

The processing unit can carry out, e.g., sequential steps of assay processes. The processing units can be programmed to carry out required inputs and outputs in the desired order. The processing units can have algorithms to calculate result outputs from sensor (electrode, photodetector, etc.) inputs. The processing units can have, e.g., digital memory to store instructions for carrying out one or more assays, and to retain data from device sensors.

Methods of Assay Cartridge Use and Manufacture

Laboratories can offer a variety of coagulation assays, e.g., in coagulation "panels", but most hemostasis or coagulation panels include the prothrombin time (PT) and activated partial thromboplastin time (aPTT) at the minimum. The combination of results from coagulation screening tests including PT, APTT, Clauss fibrinogen, and thrombin clot time (TCT) or thrombin time (TT) can be used to determine the defect in coagulation factors and pathways. Laboratory PT, aPTT, and fibrinogen tests can serve as first line (screening), and TT as second line (specific) testing for diagnosis in secondary hemostasis, as shown in table 1 (Lippi et al. Clin Chem Lab Med 2007; 45 (1):2-12) and table 2 (Perkin et. al. Pediatric Hospital Medicine: Textbook of Inpatient Management, 2008).

TABLE 1

Bleeding Disorder Diagnosis
6 Lippi et al.: Diagnostic approach to inherited bleeding disorders
Table 1 First- and Second-line and Global Coagulation Tests.

|  | First-Line Screening | Second-Line Screening |
| --- | --- | --- |
| Hemmoragic Disorders primary Hemostasis | Platelet count PFA-100 | Platelet aggregation Platelet nucleotides Platelet factor 3 (PF3) Von Willebrand factor (Ag and Functional) |
| Secondary hemostatis | Activated Partial thromboplastin time (aPTT Prothrombin time Fibrinogen (functional) | Intrinsic pathway factors Factor VII Fibrinogen (immunological) Factor XIII Thrombin time and/or reptilase time a2-Antiplasmin Plasminogen activator inhibitor-1 |
| Global (alternative) tests | Thrombin generation assays Thrombelastography/ thromboelastometry Clot waveform analysis Atomic force microscopy (AFM) |  |

TABLE 2

Bleeding Disorder Testing

First Line Testing:

CBC with Platelet Count, PT, aPTT, Fibrinogen, 1:1 mix PT, aPTT if prolonged
Von Willebrand testing (vWF:ag, vWF:Rco, FVII activity and vWF multimers).

Second Line Testing

Thrombin Time
Factor XIII activity
Platelet function analyzer 100
Platelet Aggregation The combination of features in the cartridges described herein enable 5 simplified analyses with improved technical results. The cartridges can be assembled with the flexible layers or rolled media continuously laminated, aligning features, and sealing channels, e.g., between the cover and base layers. In the assembled cartridges, fluid samples can be filtered, labeled, captured, washed, and detected with high sensitivity without external direction of fluid flows through the cartridge.

Samples can contain one or more analytes of interest. The sample can be prefiltered or centrifuged to remove particles that may block channels or obscure detection. In many embodiments, the sample is an unmodified body fluid (such as whole blood) or bioculture product. Optionally, samples can be applied directly to the cartridge having a filter in the inlet port before flowing into the cartridge channels. Samples are typically aqueous solutions or suspensions, so tend to interact with hydrophilic surfaces of the channels with stronger capillary action (lower contact angles). Alternately low contact angles can be provided for non-polar (e.g., hydrophobic) fluids by providing more hydrophobic surfaces in the cartridges. Flow rates can also be modified by changing hydrophobicity of channel surfaces and/or by changing channel dimensions.

Given a desired capillarity (flows controllable by, e.g., hydrophilicity, channel dimensions, and channel textures), the sample fluid flows along a channel (and/or to a chamber), optionally coming into contact with a reagent. The reagent can be presented on a surface, e.g., in a dissolving matrix (e.g., polyol, surfactant, etc.) that releases reagent continuously for a time to interact with analyte molecules as they flow through the zone. Alternately, the reagent can be in the form of a fluid, gel, or solid, e.g., rapidly dissolving into the sample fluid stream. In a typical embodiment, a reagent is applied to opposite walls (top/bottom and/or left/right sides) to provide rapid blending with sample fluid.

The cartridges can be manually inserted into a detection chamber of an assay device for analysis. The device can have one or more types of detectors. For example, the assay device can have contact electrodes that come into electrical contact with the contact pads of the cartridge when it is inserted onto or within the device, e.g., to detect electrical parameters (e.g., voltage, current, impedance, capacitance, resistance) from probes in channels of the cartridge. Alternately, or in addition, the assay device can be configured to interrogate and detect sample analytes using light (photometry, fluorimetry, densitometry, etc.) through transparent cartridge layers. The assay device can be, e.g., hand held or desk top; the cartridge technology allowing for small scale assay devices and/or larger scale high throughput devices. In preferred embodiments, the detector device is portable and receives the thin cartridges at any time after application of sample to the inlet (or even before). Where there is more than one analyte and/or more than one capillary channel, the device can have multiple detectors, e.g., electric and/or colorimetric.

A number of methods and compositions are discussed in the Summary of the Invention and further details are provided herein and in the Examples section. As would be readily appreciated by the skilled person, the disclosures can be read in combination.

EXAMPLES

The following examples are offered to illustrate, but not to limit the claimed invention. It is understood that the examples and embodiments described herein are for illustrative purposes only and that various modifications or changes in light thereof will be suggested to persons skilled in the art and are to be included within the spirit and purview of this application and scope of the appended claims.

Example 1—Fibrinogen Measurement

The qLabs FIB is a point-of-care coagulation test system that quantitatively determines clottable fibrinogen in capillary whole blood. It includes a handheld qLabs ElectroMeter and a fibrinogen test strip.

Figure 8A:
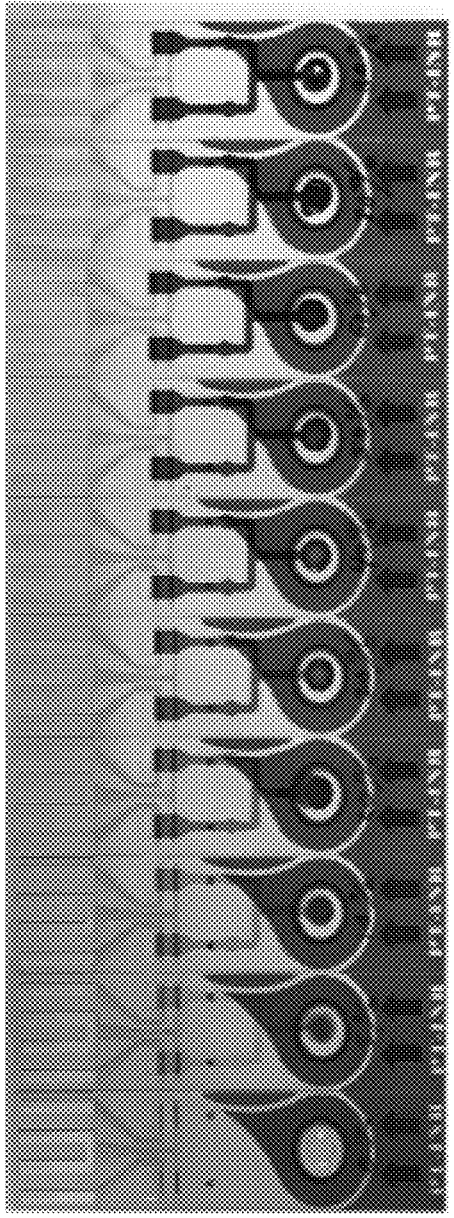
FIG. 8A shows 10 fibrinogen cartridges after analysis of samples with varying Hct values.
Figure 8B:
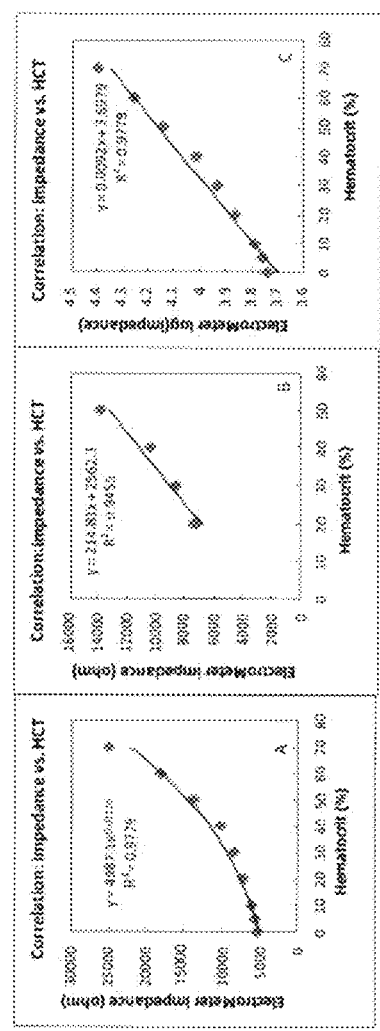
FIG. 8B shows correlation and regression analysis of impedance data from a Hct dilution series, providing a standard curve for determination of sample Hct.

To perform a fibrinogen test, a user removes a test strip from a storage pouch and inserts it into the qLabs Electrometer. The ElectroMeter automatically detects insertion of the test strip and heats the strip up to a pre-set temperature. After a drop of blood (10-15 uL) is applied to the sample well of the strip, the blood sample travels along a two-arm channel system by capillary action and stops at two ends of the channel system, e.g., as shown in FIG. 8A. There are two arms of channel that are connected to the sample well: the left arm channel is pre-coated with thrombin reagent which is brought to contact and react with the fibrinogen component of the sample. Enzymatic reactions that occur in the sample-reagent mixture result in formation of fibrin clot which impedes sample flow travelling along the channel. Such a reduction in sample flow rate is proportionally related to the concentration of both clottable fibrinogen and the amount of red blood cells present in the blood sample. In contrast, sample travelling in the right arm channel does not experience such a fibrinogen-dependent reduction in flow rate due to absence of thrombin in this arm of channel.

To determine the flow rate of the sample travelling in the channel, electrode pairs are built at ends of the two channel arms which function as two timers to register the now times elapsed for the sample to reach to the channel ends. To exclude the contribution of the red blood cell part to the reduction of sample flow rate, electrode pair on the right arm channel also serves to measure the hematocrit levels of the sample (i.e., red blood cell content) by an electrical impedance method, as there is an excellent linear relationship between hematocrit level and electrical impedance of the sample ($R2=0.94$, for hematocrits 10-52%. Data is not shown). With this built-in capability of hematocrit measurement, the qLabs ElectroMeter software calculates the plasma fibrinogen concentration value, in g/L, according to the hematocrit-adjusted flow time value and calibration coefficients, e.g., as determined from the processor readable strip code.

The flow time of sample is proportional to the concentration of clottable fibrinogen present in sample, e.g., as shown in the chart presented in Example 6, below.

Example 2—A New Method of Determining Fibrinogen

The standard Clauss method fibrinogen assay is essentially a thrombin time assay wherein plasma is diluted 10-15× so that there is excess thrombin and fibrinogen is the rate limiting reactant in the coagulation. The fibrinogen assays provided by our cartridges provide the substantial benefit of determining fibrinogen directly from whole blood, e.g., without requiring separation or dilution of plasma before the test.

The present methods consume sample fibrinogen in way reflecting the fibrinogen concentration, without requiring dilution. The FIB system is a fibrinogen test working in a way that differing significantly from that by Clauss method. Both tests end with a fibrin clot made from fibrinogen. However, the Clauss method involves measuring the rate of clot formation or clotting time in a 10 or 15 times diluted sample under influence of excess thrombin (e.g., 100 IU/mL), whereas the method of this invention measures density of a clot in an undiluted sample that is formed alongside with a channel coated with excess thrombin (e.g., 3000 IU/mL).

Because the thrombin reagent is presented in excess in the Clauss method, the fibrinogen content becomes rate limiting. Thus, the clotting time can be used to measure concentration of the fibrinogen. In the method of this invention, the thrombin reagent is coated excessively on the inner wall of the channel, so it can also function as a fibrinogen "consumer" to deplete the flowing-in fibrinogen content via clot formation alongside the channel. This has an effect similar to diluting of the sample to such an extent that fibrinogen concentration is the rate limiting reaction constituent.

We have shown that the higher the content of fibrinogen in a sample, the denser the clot that is formed inside the channels, and thus slower flow of the sample in channels. When testing whole blood samples, the contribution of red cells to the density of the clot is eliminated (e.g., using Hct determination and compensating calculations) so that a determined sample flow rate is the function of fibrinogen content alone. We have introduced a built-in hematocrit adjustment algorithm that is proven to be effective in deconvoluting the impact of hematocrit on our whole blood fibrinogen test system.

Figure 11A:
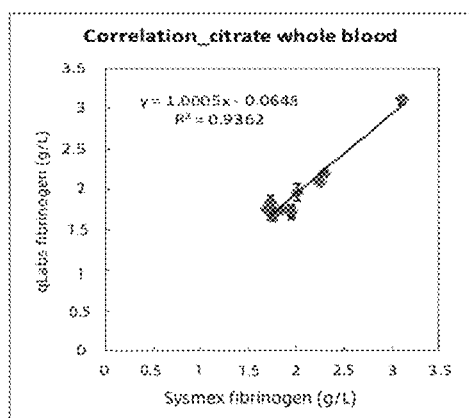
FIG. 11A presents data showing haw a presently described fibrinogen cartridge correlates with a standard fibrinogen assay, while FIG. 11B demonstrates that the present fibrinogen assay is distinguished from a standard thrombin time (TT) assay.
Figure 11B:
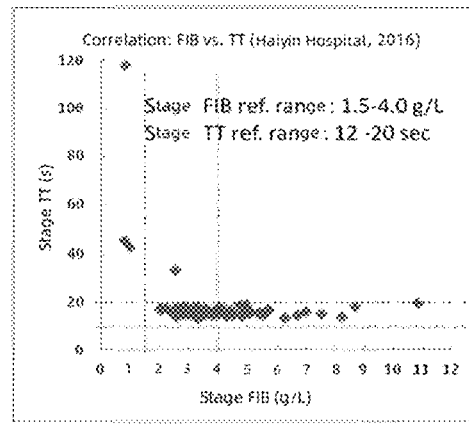

Our fibrinogen test, thus configured, should not be considered a thrombin time. Our whole blood fibrinogen assay can measure fibrinogen concentrations, e.g., in the range of 1.0-3.5 g/L, while the standard thrombin time fails to correlate with samples fibrinogen levels in range of 1.5-3.5 g/L, e.g., as shown in the charts of FIG. 11. For example, the Sysmex fibrinogen assay correlates well with our qLabs fibrinogen assay, as shown in the chart 11 A. In contrast, no such correlation was found when comparing the Stage TT assay, as shown in FIG. 11B.

Example 3—Design of qLabs Coag Panel 4

The qLabs Coag Panel 4 (CP4) is an extension of the qLabs PT/aPTT Combo product. It can be performed on a qLabs ElectroMeter that is modified with a new strip connection design and software capable of testing PT, aPTT, FIB, and TT all with one drop of capillary whole blood sample. The CP4 strip includes one electrode layer 60 and two channel layers (61 and 62) which are laminated to form a sandwich structure, as shown in FIG. 6.

In this sandwich design, the two sided electrode layer includes one set of electrodes on the front side and another set on the back side. The front electrodes serve to detect PT and aPTT coagulation reactions while the back side electrodes are used to measure FIB and TT. There are two channel layers which are PT 63/aPTT 64 and FIB 65/TT 66. In PT/aPTT channels, PT and aPTT reagents are deposited on the left and right reaction chambers, respectively; in FIB/TT channels, the FIB reagent is deposited on the left arm of the channels while the TT reagent on the right reaction chamber. After lamination of the channel layers to the electrode layer, four channels, i.e., PT, aPTT, FIB, and TT channels, are formed with four air vent holes 67 positioned at the end of the channels.

Figure 16:
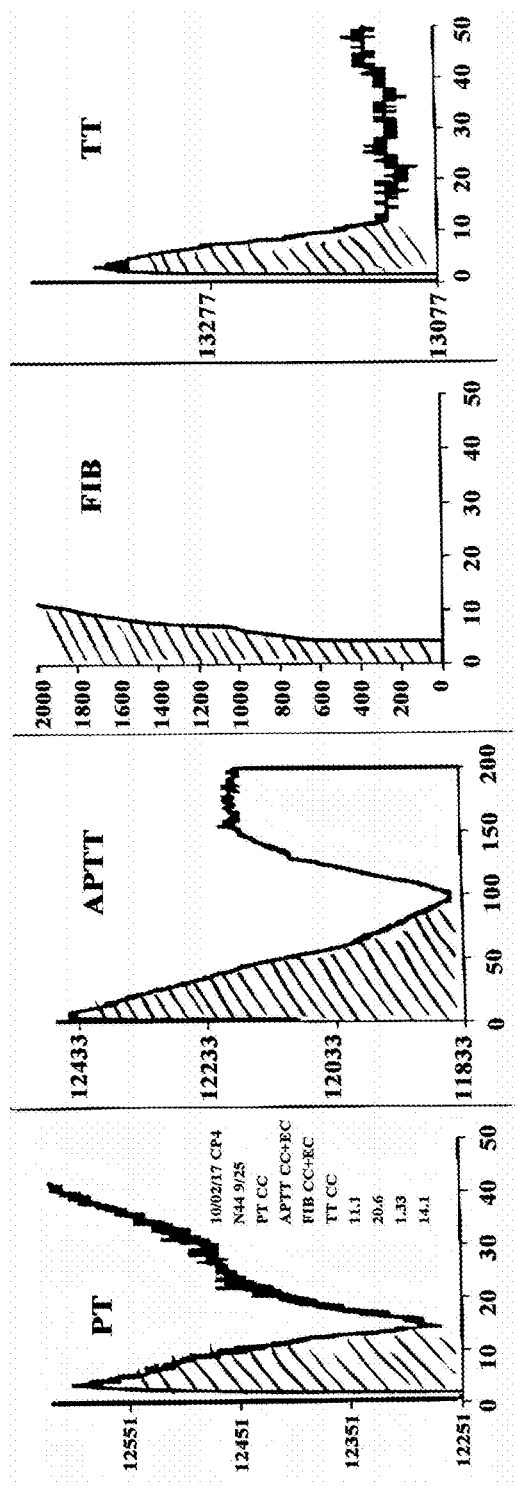
FIG. 16 presents charts showing typical impedance/time course curves where shaded areas indicate parts of the curves used for calculating the clotting times for PT, aPTT, and TT channels and flow rate for the FIB channel.

To perform a 4-in-1 test of PT, aPTT, FIB, and TT from one drop of blood sample, one CP4 strip is inserted into the CP4 ElectroMeter, which automatically detects insertion of the strip and heats the strip up to a pre-set temperature. When a blood drop is added to the sample well of the strip, it flows across channel surfaces to reconstitute appropriate reagents for assays in each channel. The sample reacts with the reagents of PT, aPTT, and TT to form clots in the three reaction chambers. For the FIB analysis, thrombin near the proximal channel end begins formation of fibrin to slow flow as its progress is timed to the distal timing gate electrodes. The ElectroMeter detects and monitors changes of electric current or electrical impedance across the three electrode pairs and determines the clotting times for PT, aPTT, TT channels, and flow rate for the FIB channel. Fee FIG. 16. The monitored values are used to calculate coagulation parameter values. The charts below show typical impedance/time course curves where shaded areas indicate parts of the curves used for calculating the clotting times for PT, aPTT, and TT channels and flow rate for the FIB channel.

To determine the FIB levels of the blood sample, flow rate (or flow time), rather than clotting time, of the sample flowing through the channels is employed, as described herein.

Example 4—Detection and Calculation of Hct Factor

We evaluated variability of our hematocrit measurement system using mixtures of centrifuged red blood cells and citrate plasma with different volume ratios ranging from 0 to 60%, which corresponds to hematocrit range of 0% to 60%. We added the mixtures into reagent-free qLabs PT test strips for electrical impedance measurement with multiple meters. As shown in FIG. 8A, the blood mixtures were added to 10 strips for Hct analysis. Table and figures below show the results of 3 replicate qLabs tests on 7 whole blood samples with hematocrit of 0%, 10%, 20%, 30%, 40%, 50% and 60%.

| Plasma/ RBC ratio | HemoPoint Hb [g/dL] | Microtube Hct [%] | Q-2 meter # | Test 1 AD | Test 2 AD | Test 3 AD | Mean AD | Stdev AD | CV AD |
|---|---|---|---|---|---|---|---|---|---|
| 100/0 | 0 | 0 | 1 | 869 | 876 | 842 | 857 | 20 | 2.3% |
|  |  |  | 2 | 875 | 849 | 828 |  |  |  |
| 90/10 | 3.0 | 10.0 | 3 | 789 | 747 | 797 | 779 | 28 | 3.6% |
|  |  |  | 4 | 802 | 739 | 800 |  |  |  |
| 80/20 | 5.9 | 19.7 | 5 | 692 | 662 | 691 | 680 | 23 | 3.4% |
|  |  |  | 6 | 707 | 643 | 683 |  |  |  |
| 70/30 | 9.3 | 30.0 | 7 | 627 | 596 | 605 | 606 | 15 | 2.4% |
|  |  |  | 8 | 612 | 585 | 613 |  |  |  |
| 60/40 | 12.7 | 40.0 | 9 | 520 | 494 | 508 | 509 | 11 | 2.1% |
|  |  |  | 10 | 521 | 499 | 509 |  |  |  |
| 50/50 | 15.4 | 50.8 | 11 | 454 | 446 | 450 | 449 | 7 | 1.5% |
|  |  |  | 12 | 455 | 437 | 454 |  |  |  |
| 40/60 | 17.8 | 59.4 | 13 | 378 | 369 | 375 | 378 | 6 | 1.7% |
|  |  |  | 14 | 382 | 374 | 387 |  |  |  |

Mean CV: 2.4%

To accommodate the double-sided electrodes and contact pads of the CP4 strip, the previous qLabs ElectroMeter single-sided electrodes assay device contacts are modified to incorporate another set of electrical contacts oriented to contact the back side contact pads of the cartridge. This modification enables, e.g., simultaneous monitoring of electrical impedance changes that occur across all the four electrode pairs of the CP4 strip.

Figure 17:
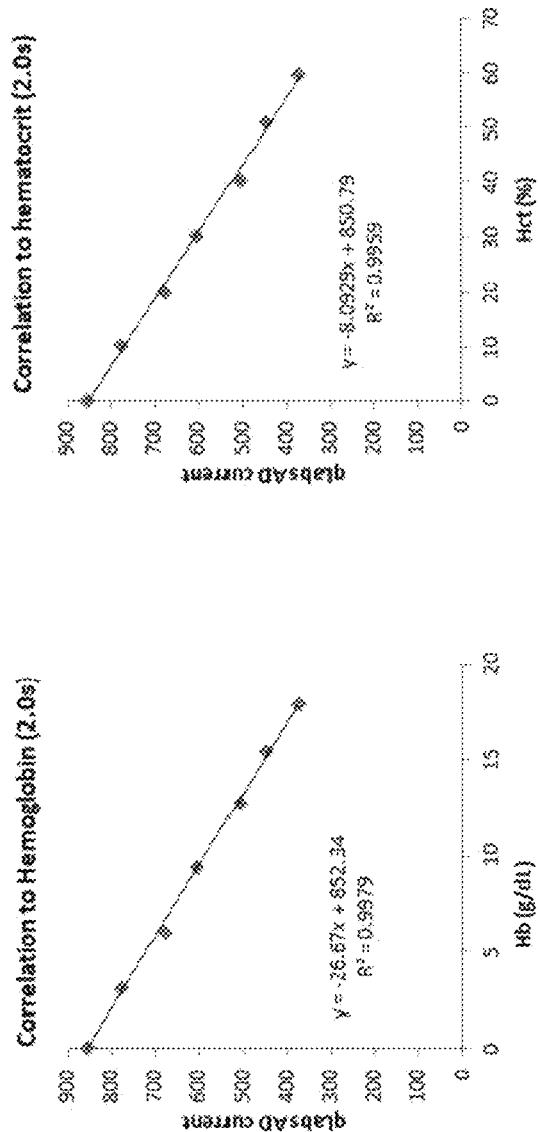
FIG. 17 presents charts showing current magnitude in an electrometer decreases with the increasing hemoglobin concentration and red blood cells content or hematocrit level.

As can be seen in FIG. 17, the current magnitude decreases with the increasing hemoglobin concentration and red blood cells content or hematocrit level. Inter-test variability in current measurement is low with an average CV of well below 5.0%. Using Ohm's Law, we convert the current values into the impedance ones with a meter factor of 19131050 for this electrometer.

Example 5—Detection of Abnormal Fibrinogen

Figure 9A:
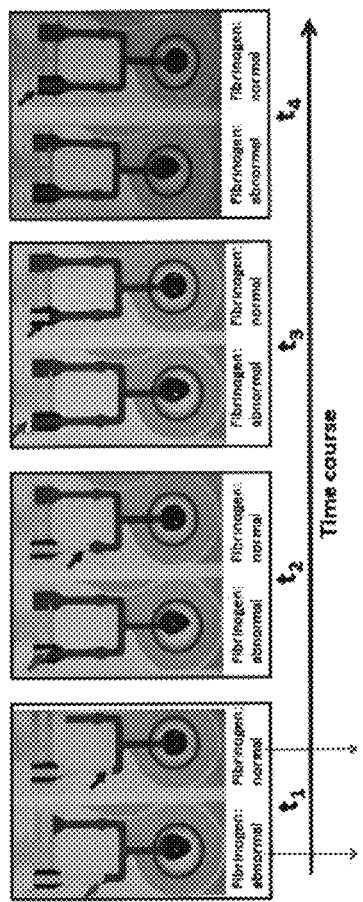
FIGS. 9A and 9B show images of normal and abnormal fibrinogen in the test channels of a fibrinogen assay.

The present methods and systems can distinguish between normal and abnormal fibrinogen in a sample. FIG. 9A shows a time sequence of sample flow in a FIB cartridge for samples having normal and abnormal fibrinogen. Even though the amount of fibrinogen in each sample is substantially the same (e.g., by ELISA assay) the FIB cartridge provides a functional result wherein a sample with functional fibrinogen has a longer flow time than for a sample with an equivalent amount of abnormal fibrinogen.

Figure 9B:
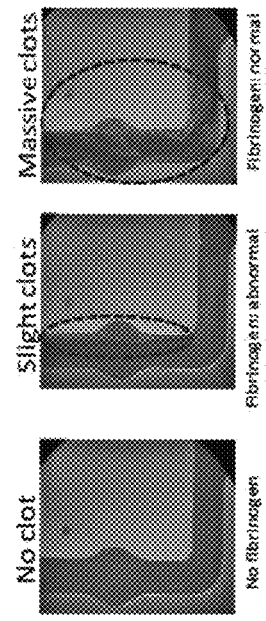
Figure 10A:
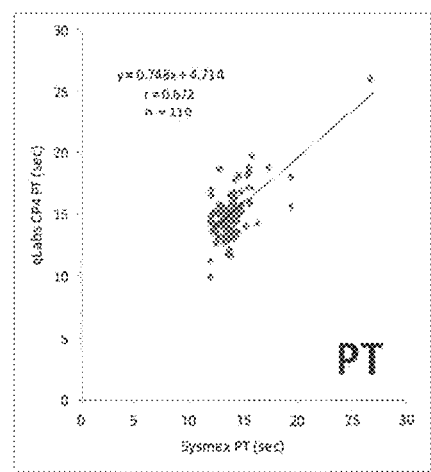
FIGS. 10A to 10D show four correlation charts demonstrating correlation of PT, aPTT, fibrinogen, and TT coagulation panel values to old art reference values.
Figure 10B:
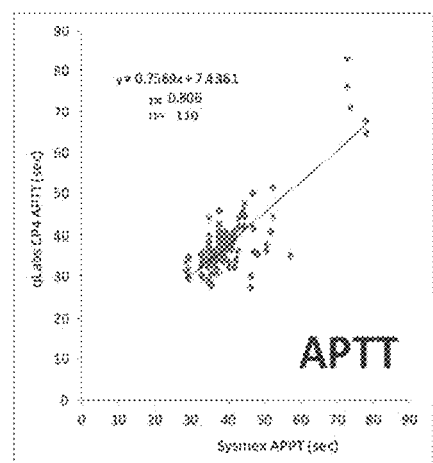
Figure 10C:
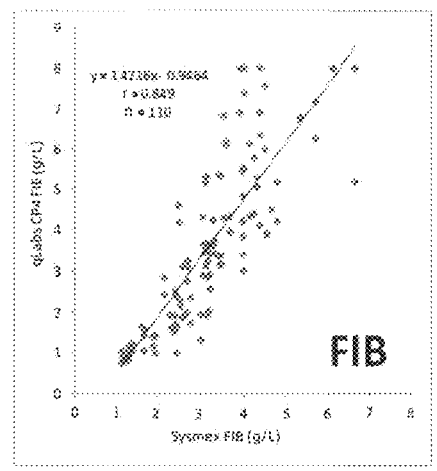
Figure 10D:
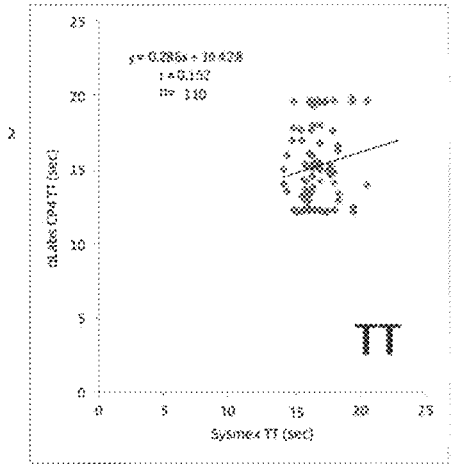

FIG. 9B shows close up views of the test (thrombin positive) cartridge channel for samples with no fibrinogen, abnormal fibrinogen, and normal fibrinogen. Note that slight clot with abnormal fibrinogen, and substantial clotting with the normal fibrinogen. The abnormal fibrinogen is apparent in the sample flow rate and appearance of the sample in the channel.

Figure 18:
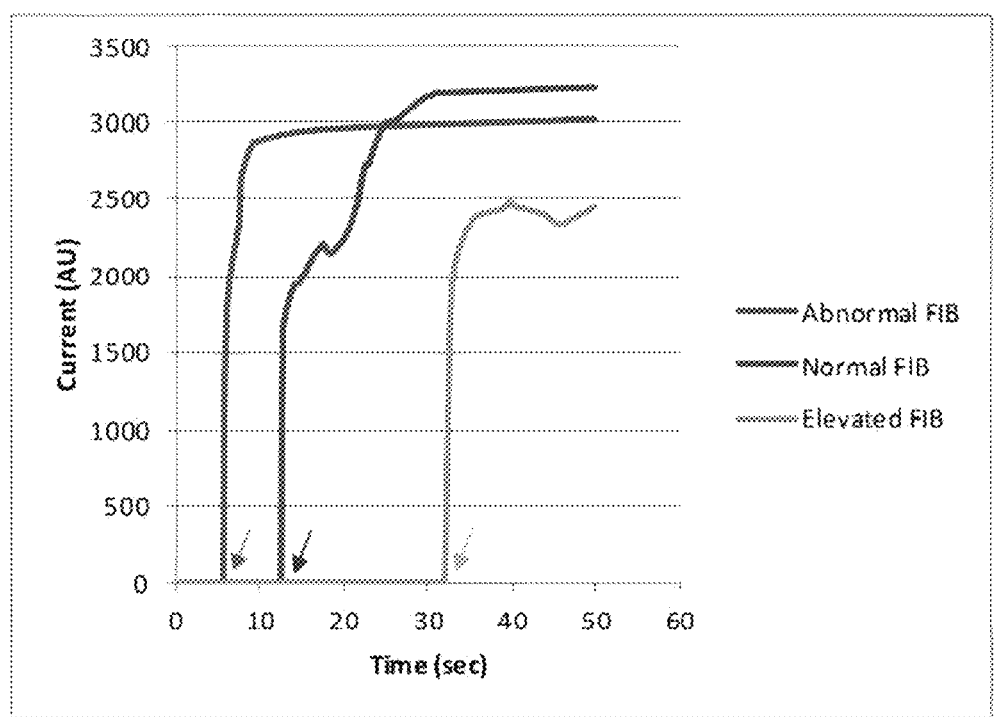
FIG. 18 shows the electric current/time-course curves as detected across the electrode pair as fibrinogen clots in a channel.

FIG. 18 shows the electric current/time-course curves as detected across the electrode pair of the FIB channel, illustrating that the flow time of sample is directly proportional to the concentration of clottable fibrinogen present in sample. Determination of the flow times can be realized by calculating current thresholds or first order derivatives of the current/time-course curves.

These experiments and data show that the FIB cartridge is capable of detecting and determining fibrinogen parameters in a number of useful ways (e.g., abnormal activity, concentration, viscosity, light absorbance, image, electrical resistance, etc.).

Example 6—Methods and Materials for 4-Assay Cartridge

Contents of Reagents:
PT: human recombinant thromboplastin, stabilizers, preservatives and additives.
aPTT: micronized silica, phospholipids, stabilizers, preservatives and additives.
FIB: bovine thrombin, buffer, stabilizers, preservatives and additives.
TT: bovine thrombin, buffer, stabilizers, preservatives and additives.

Fabrication of Strips:
Dispense PT reagents on PT channels in dot pattern using Biodot dispenser.
Dispense aPTT reagents on aPTT channels in coating pattern with Biodot dispenser.
Dispense FIB reagents on FIB channels in coating pattern using Biodot dispenser.
Dispense TT reagents on TT channels in coating pattern using Biodot dispenser.
Dry reagents deposited on channels.
Laminate channels parts to electrode parts using lamination machine and pressing machine.
Slice the laminated parts to generate individual strips.
Seal strips in individual pouches that contains desiccant.
Store strip pouches at room temperature.

Preparation of whole blood samples for analytical performance evaluation:
PT and aPTT samples: prepare citrate whole blood using Alsever's solution washed red blood cells and Siemens coagulation control plasma, Level 1, 2 and 3 (plasma: red blood cells=3:2 v/v).
FIB and TT samples: prepare citrate whole blood containing different levels of fibrinogen and constant 40% of red blood cells. Plasma with different levels of fibrinogen is derived from abnormal level by using Siemens fibrinogen control, normal level by Siemens normal control, and elevated level by spiking lyophilized fibrinogen protein to normal control.

Test of qLabs CP4 with citrate whole blood samples:
For citrate whole blood samples, re-calcify the samples by adding 15 uL added 75 mM CaCl2 to 100 uL of citrate sample.
Transfer 20 uL of re-calcified sample to sample well to initiate test.

Results:
In-house test of CP4 with citrate whole blood samples:

|  | Siemens coag control level 1 | Siemens coag control level 2 | Siemens coag control level 3 | Siemens FIB abnormal | Siemens FIB normal |
|---|---|---|---|---|---|
| CP4 test |  |  |  |  |  |
| PT, sec | 12.5 | 33.5 | 57.8 | 12.3 | 13.1 |
| aPTT, sec | 33.2 | 52.1 | 77.5 | 34.3 | 31.5 |
| FIB flow time, sec | 5.7 | 5.9 | 5.1 | 5.5 | 12.5 |
| TT, sec | 7.5 | 8.5 | 6.3 | 12.1 | 6.7 |
| Sysmex CA-500 |  |  |  |  |  |
| PT, sec | 10.5 | 26.9 | 45.3 | 10.4 | 10.9 |
| aPTT, sec | 28 | 48.8 | 71.9 | 28.4 | 29.1 |
| FIB, g/L | 2.11 | 2.22 | 2.17 | 1.01 | 2.26 |
| TT, sec | 12.7 | 13.2 | 12.5 | 26.7 | 13.1 |

As can be seen from the table, the results of CP4 PT, aPTT, FIB, and TT correlated well to those by the laboratory method which is the Sysmex CA-500. As can be seen from the regression charts of FIGS. 10, the qLabs CP4 demonstrated reasonably well clustered correlations in PT, aPTT, fibrinogen, and TT with the laboratory method (Sysmex). Note from charts 10A PT, 10B aPTT, 10C FIB, and 10D TT, the CP4 results and standard assay results clustered fairly closely, typically with a roughly 1:1 correlation. Even where the assay times are not exactly the same, the results can be standardized, e.g., based on a determined constant or other algorithm.

Conclusion: The qLabs CP4 is novel point-of-care coagulation test system that can quantitatively determine prothrombin time, activated partial thromboplastin time, fibrinogen and thrombin time with one drop of capillary blood in less than 420 seconds.

Example 7—Dual Fibrinogen Assay Cartridge with Replicate Determinations

Figure 12:
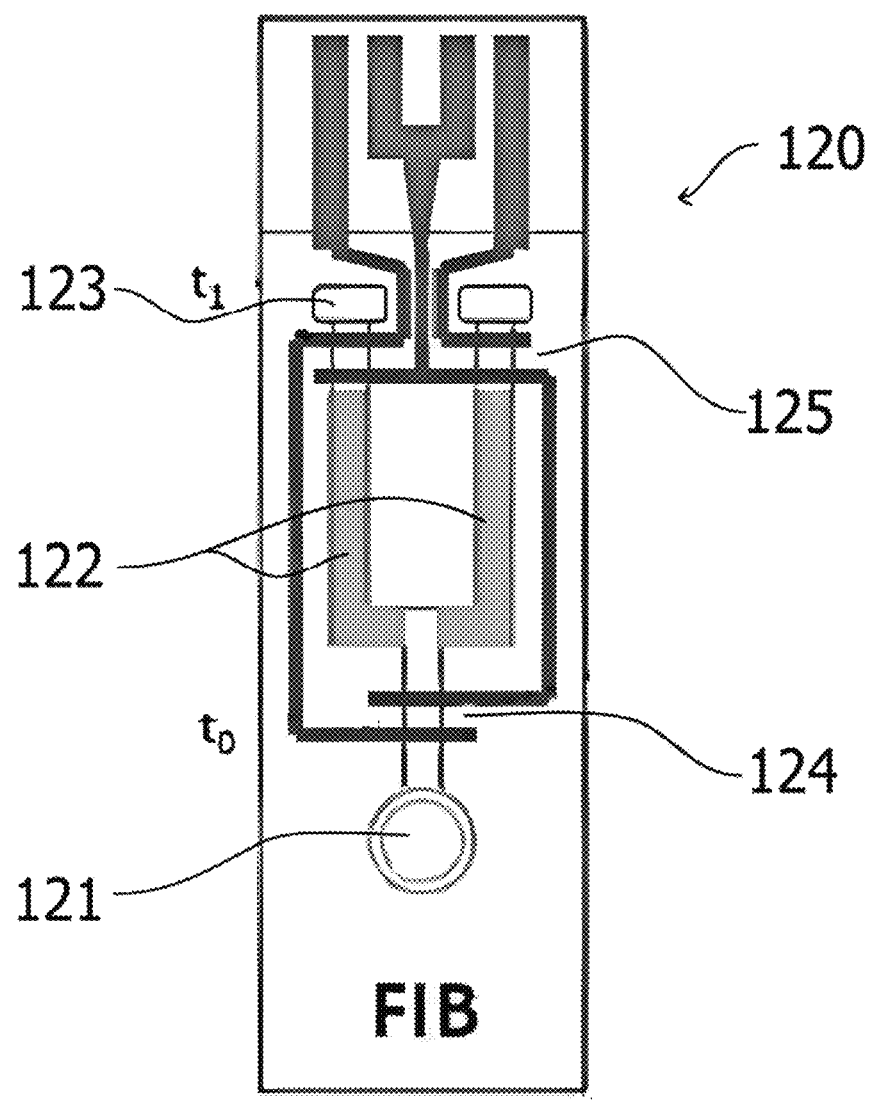
FIG. 12 is a schematic diagram presenting a dual fibrinogen assay to provide replicate results for a single sample.

A fibrinogen assay cartridge, as shown in FIG. 12, can provide replicate determinations, e.g., for quality control and enhanced precision. The dual fibrinogen design cartridge 120 provides a pair of fibrinogen assay channels 122, e.g., similar in function to those of FIG. 1.

The dual fibrinogen cartridge design can provide fibrinogen and hematocrit determinations using timing gates and impedance electrodes along a pair or lateral flow channels. The dual fibrinogen cartridge 120 includes a sample inlet port 121 in fluid contact through lateral flow channels 122 to vent 123. Sample can be applied to inlet 121 and flow along channels 122, coming in contact with timing start gate 124 electrodes to start a flow timing sequence. Further, the impedance across the timing gate electrodes in the presence of the sample is related to the amount of particles in the sample and can be detected to determine, e.g., a hematocrit of a whole blood sample. The time it takes the fluid (e.g., whole blood) sample to flow through the channels can be marked by contact of the fluid with the electrodes at end timing gates 125.

In use we can measure both the clot time (correlated with fibrinogen concentration) and hematocrit in the twin mono-channel strip design. Table and figures below show the results of testing 1:1 (v/v)—diluted citrate whole blood samples (Sysmex fibrinogen 4.5 g/L) with Hct levels of 10%, 20%, 30%, 40%, 50% and 60%.

| Sample # | Plasma/RBC (v/v) | qLabs Hct, % | Flow time 1 | Flow time 2 | Mean time | log (time) | Hct Factor 100/(100 − Hct) | Adjusted log (time) = log(time) × Hct |
|---|---|---|---|---|---|---|---|---|
| 1 | 90/10 | 11.5 | 167.8 | 189 | 178.4 | 2.25 | 1.13 | 2.54 |
| 2 | 80/20 | 22.0 | 123.6 | 101 | 112.3 | 2.05 | 1.28 | 2.63 |
| 3 | 70/30 | 30.1 | 67 | 80 | 73.5 | 1.87 | 1.43 | 2.67 |
| 4 | 60/40 | 40.5 | 35.6 | 48.6 | 42.1 | 1.62 | 1.68 | 2.73 |
| 5 | 50/50 | 51.6 | 20 | 19.2 | 19.6 | 1.29 | 2.07 | 2.67 |
| 6 | 40/60 | 58.8 | 10.2 | 14.4 | 12.3 | 1.09 | 2.43 | 2.65 |

Figures 19A, 19B:
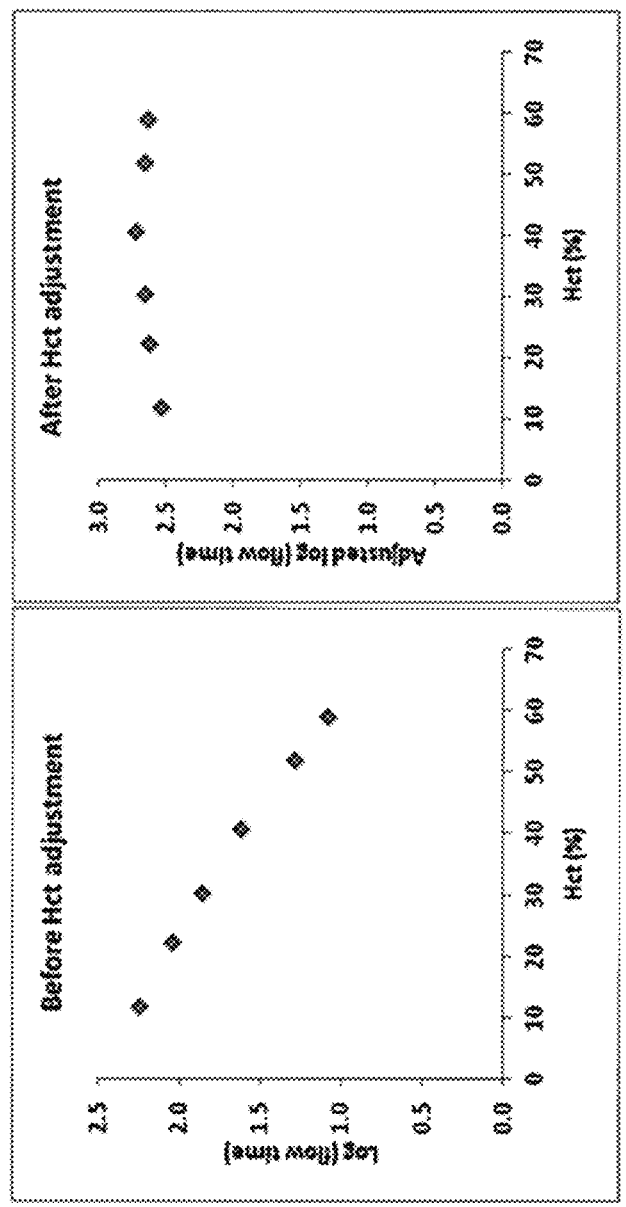
FIGS. 19A and 19B show charts for flow time of the samples decreasing proportionally with increase in hematocrit of the samples.

As can be seen in FIGS. 19A and 19B, the flow time of the samples decreases proportionally with increase in hematocrit of the samples because less fibrinogen in samples with higher levels of hematocrit. As note, dilution of whole blood sample by one fold or larger can drastically reduce the flow impedance effect of red cells on flow rate of this system (data not shown). After adjusted by volume exclusion factor of the red cells which is 100/(100−Hct), the flow time is found to be nearly independent of hematocrit levels over the range from 10% to 60%, suggesting validity of hematocrit correction for obtaining accurate fibrinogen measurement with this system.

Figures 20A, 20B:
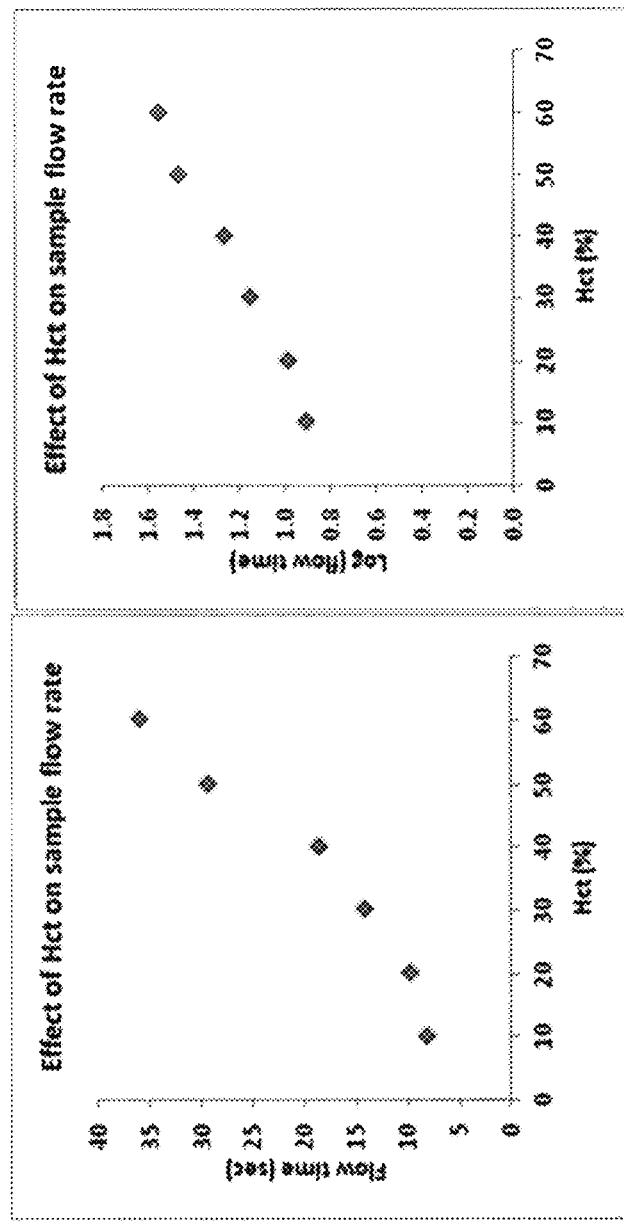
FIGS. 20A and 20B show the effect of hematocrit on sample flow rate as fibrin is formed in a channel in the presence of a thrombin reagent.
Figures 21A, 21B:
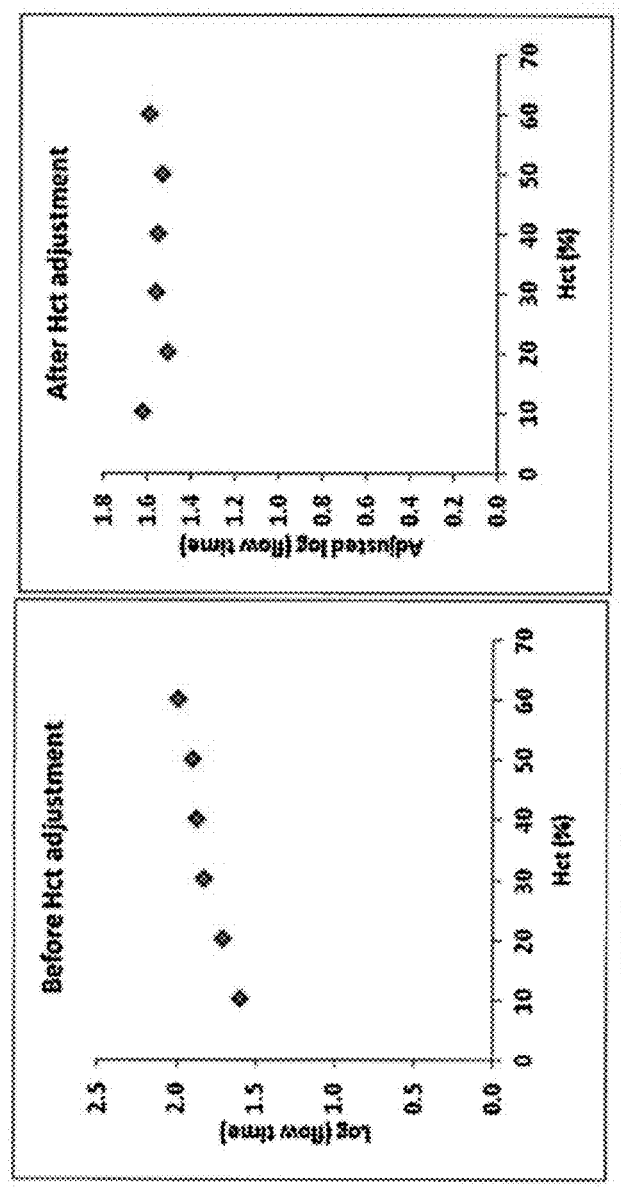
FIGS. 21A and 21B show the results of testing non-diluted citrate whole blood samples (Sysmex fibrinogen 2.5 g/L) with Hct levels of 10%, 20%, 30%, 40%, 50% and 60%.

When testing a whole blood sample with 10% dilution, e.g. citrate anticoagulated sample, or a sample without any dilution, such as capillary and fresh venous blood, it is found that the red cell particles drastically impede the flow of the samples in the channel with thrombin reagent, as shown in FIGS. 20A and 20B. This now impedance effect of red cells can be used to adjust the flow rate of such whole blood samples even though to a lesser extent as compared with the case of highly diluted sample as illustrated above. Table below and FIGS. 21A and 21B show the results of testing non-diluted citrate whole blood samples (Sysmex fibrinogen 2.5 g/L) with Hct levels of 10%, 20%, 30%, 40%, 50% and 60%:

| Sample # | Plasma/RBC | qLabs Hct, % | Flow time 1 | Flow time 2 | Mean time | log (time) | Hct Factor Log(10*Log(Hct)) | Adjusted log (time) = Log (time)/ Hct factor |
|---|---|---|---|---|---|---|---|---|
| 1 | 90/10 | 9.4 | 44 | 37 | 40.5 | 1.61 | 0.99 | 1.63 |
| 2 | 80/20 | 23.4 | 55 | 49 | 52.0 | 1.72 | 1.14 | 1.51 |
| 3 | 70/30 | 29.8 | 66 | 70 | 68.0 | 1.83 | 1.17 | 1.57 |
| 4 | 60/40 | 42.1 | 76.4 | 77 | 76.7 | 1.88 | 1.21 | 1.56 |
| 5 | 50/50 | 53.0 | 86.9 | 74.7 | 80.8 | 1.91 | 1.24 | 1.54 |
| 6 | 40/60 | 60.6 | 114 | 85.1 | 99.6 | 2.00 | 1.25 | 1.60 |

Contrary to the case of testing one-fold diluted whole blood sample, the flow rate of testing this 10%-diluted whole blood sample show increases with hematocrit levels of the sample. Thus, the corrected flow time is obtained by dividing the raw flow time by a hematocrit factor which is a minor adjustment in magnitude, e.g., log (10*log (Hct)). This may be explained by the counter effect of hematocrit on flow rate of such a system: the higher hematocrit level, the less fibrinogen and lower viscosity or reduced flow time the sample has; meanwhile, higher hematocrit level means more impeded flow of sample and thus increased flow time of the sample. The net effect of higher hematocrit on this measurement system will be dependent on extension of sample dilution which can be experimentally determined and factored into measurement adjustment.

Example 8—Dual Fibrinogen Assay Cartridge with High/Low Range Layers

A single multi-layer cartridge can include paired fibrinogen channels on two levels to accurately measure fibrinogen across two concentration ranges. For example, two channels (e.g., upper layer channels) can include a lower content of thrombin to shift the accurate measurement range to confidently measure samples with lower active fibrinogen content, while two other channels (e.g., lower layer channels) can include a relatively higher thrombin content to shift the accurate measurement range to confidently measure samples with relatively higher active fibrinogen content. When thrombin of high content is loaded in channels, sample now may stop in the middle of reagent-coated channels due to excessive clot formation before reaching to the upper electrode timer, limiting measurement range of the system. However, use of a higher thrombin content facilitates sensitive detection of fibrinogen in sample at very low levels.

Figure 13:
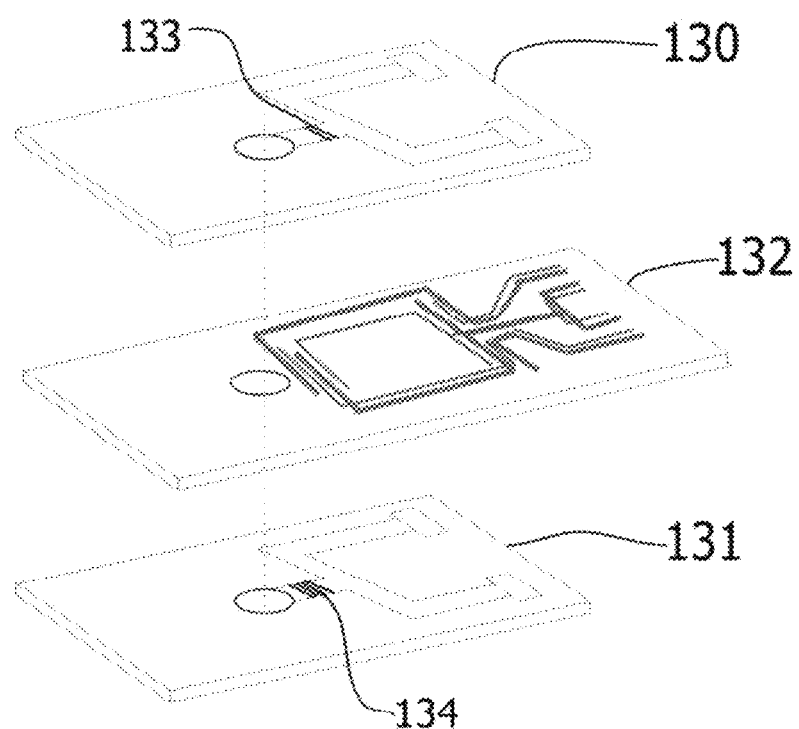
FIG. 13 is a schematic diagram showing an embodiment of a fibrinogen cartridge configured to test samples in duplicate for each of a high range and low range of fibrinogen concentrations.
Figure 22:
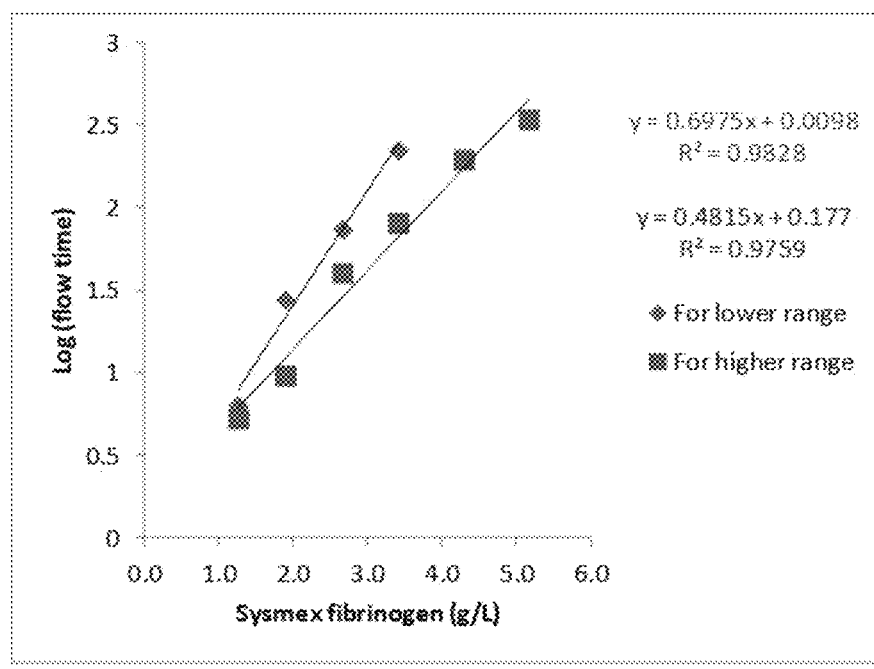
FIG. 22 presents a chart showing regression analysis on a dual fibrinogen assay with high/low range achieved on such a multi-layer cartridge using different thrombin reagent levels. Such cartridges can allow evaluation of data with either higher sensitivity or data with a higher upper limit of detection.

FIG. 13 shows an expanded view of a multilayer cartridge. Upper 130 and lower 131 channel layers sandwich a two-sided electrode layer 132. The upper layer channels can have a lower concentration of thrombin reagent 133, while the lower layer has a higher concentration of thrombin reagent 134. FIG. 22 shows regression analysis on a dual fibrinogen assay with high/low range achieved on such a multi-layer cartridge. Notice that for higher range measurement, smaller regression slope (0.4815 vs. 0.6975) is obtained due to less assay sensitivity when less thrombin reagent is used in cartridge channels, while more sensitive assay has compromised upper limit of detection. As a result, integration of high and low range assay elements into one single multi-layer cartridge device facilitates shifting the measurement range from 1.1-3.4 g/L to 1.1-5.5 g/L without changing width dimension of the cartridge receiver for the electrometer.

Example 9—Cartridge with Pretreatment Zones

Interfering substances in a patient blood sample can cause inaccurate (e.g., low) coagulation assay results. To counter the interference (e.g., due to heparin, platelets, fibrin degraded products, tranexamic acid, acidosis, hypocalcemia, etc.), the patient sample can flow aver a pretreatment zone before passing into the assay channel(s).

Figures 14A, 14B:
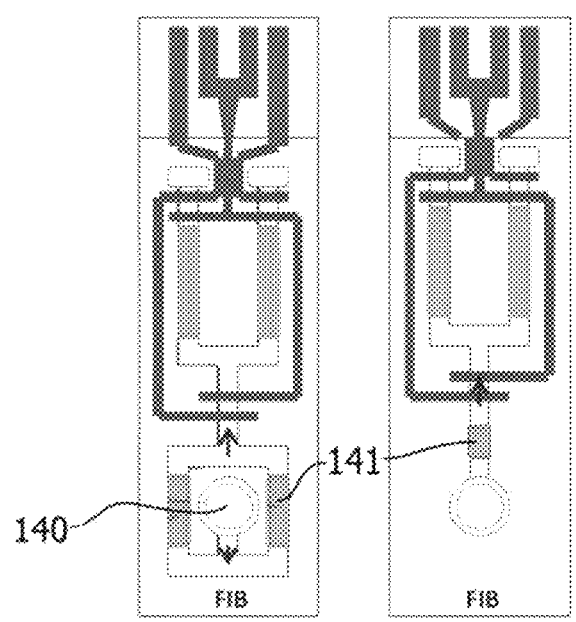
FIGS. 14A and 14B present fibrinogen cartridges having pretreatment zones with reagents to neutralize interfering substances.
Figure 15:
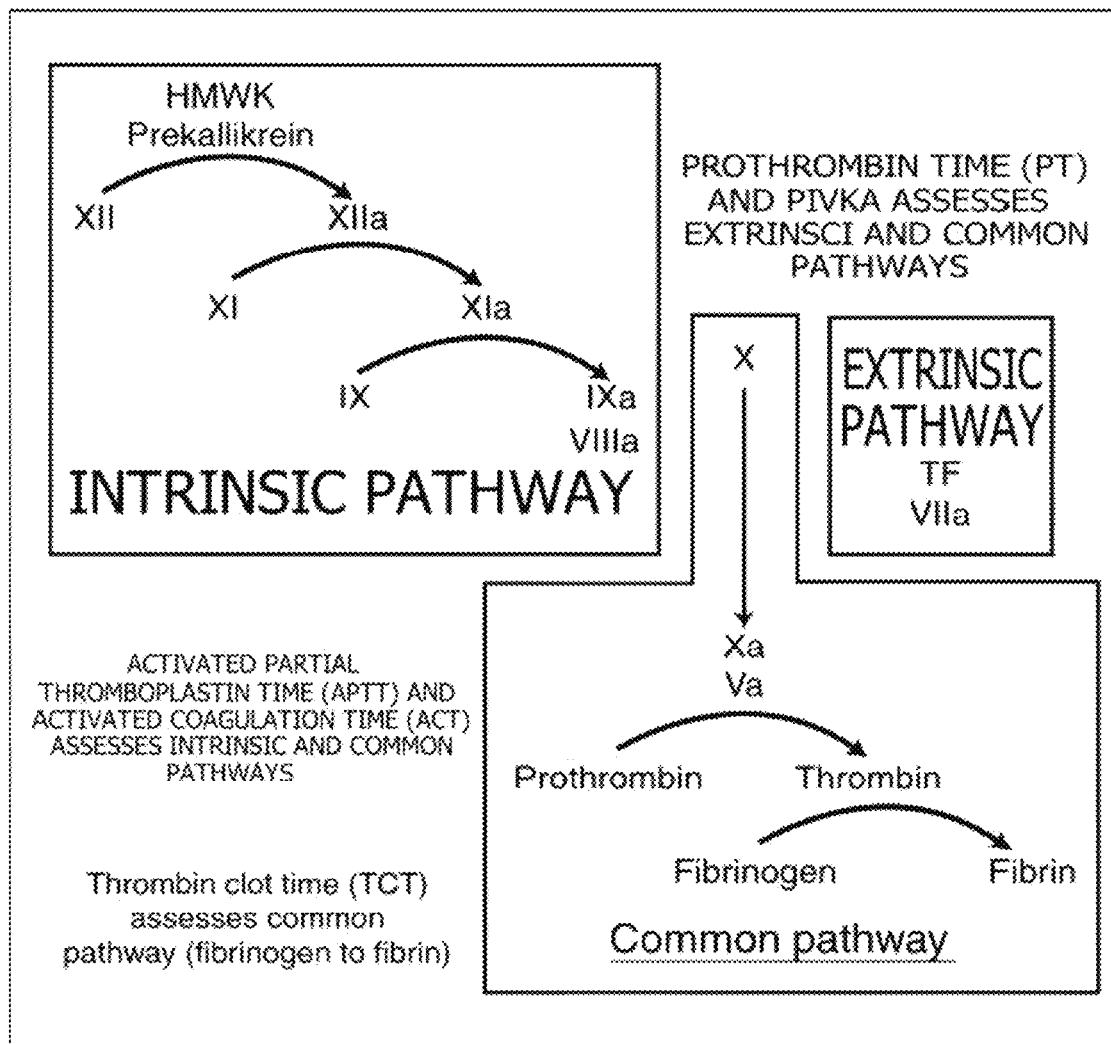
FIG. 15 is a chart presenting intrinsic, extrinsic, and common pathways to clot formation.

For example, as shown in FIG. 14A, sample applied to inlet 140 can initially flow left and right to come into contact with reagents 141 to neutralize inhibitors that may result in a low fibrinogen determination for the sample. For example, the reagents can include polybrene to neutralize heparin and abciximab to inhibit platelet activation. The reagents can be located in separate reagent zones or in a single pretreatment reagent zone, e.g., as shown in FIG. 14B.

While the foregoing invention has been described in some detail for purposes of clarity and understanding, it will be clear to one skilled in the art from a reading of this disclosure that various changes in form and detail can be made without departing from the true scope of the invention. For example, the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A fibrinogen assay cartridge comprising:
   a first channel comprises thrombin;
   a second channel;
   a sample inlet in fluid contact with the first channel and the second channel;
   an inlet channel comprising a starting electrode in contact with the inlet channel and located between the sample inlet and the thrombin;
   wherein the first channel further comprises a timing electrode adapted to determine a time taken for a sample fluid to flow from the starting electrode to the timing electrode so as to determine an amount of fibrinogen in the sample fluid; an
   wherein the second channel comprises a pair of electrodes adapted to detect an impedance or a resistance of the sample fluid so as to determine an amount of particles in the sample fluid,
   whereby the impedance or the resistance measured across the pair of electrodes is proportional to the amount of the particles in the sample fluid, and the time for the sample fluid to flow to the timing electrode is inversely proportional to the amount of fibrinogen in the sample fluid.

2. The cartridge of claim 1, wherein the first channel, the second channel and the inlet channel are lateral flow channels.

3. The cartridge of claim 1, wherein the inlet channel flows from the sample inlet and branches to the first and second channels.

4. The cartridge of claim 1, wherein the cartridge further comprises a control timing electrode that is located parallel to the timing electrode in a control channel with no thrombin and comprises the starting electrode between the inlet and control timing electrode, whereby flow of sample can be detected and timed as it flows between the start and control timing electrodes.

5. The cartridge of claim 1, wherein the second channel comprises no thrombin.

6. The cartridge of claim 1, wherein the sample comprises whole blood, whole blood from a finger stick, whole blood without anticoagulant, or whole blood anticoagulated with citrate.

7. The cartridge of claim 1, wherein the thrombin is coated onto both a top and a bottom of the first channel.

8. An assay device comprising a processing unit and the cartridge of claim 1;
   wherein the starting electrode, the timing electrode, and the pair of electrodes are in electrical contact with the processing unit, in which the processing unit detects the impedance parameter from the pair of electrodes and determines a percent of particles in the sample; or wherein the processing unit detects a fluid front of the sample contacting the starting and timing electrodes to determine a fibrinogen value for the sample.

* * * * *